United States Patent [19]

McGarry et al.

[11] Patent Number: 4,509,518

[45] Date of Patent: Apr. 9, 1985

[54] APPARATUS FOR APPLYING SURGICAL CLIPS

[75] Inventors: Richard A. McGarry, Norwalk; Douglas G. Noiles, New Canaan, both of Conn.

[73] Assignee: United States Surgical Corporation, Norwalk, Conn.

[21] Appl. No.: 349,584

[22] Filed: Feb. 17, 1982

[51] Int. Cl.³ .............................................. A61B 17/04
[52] U.S. Cl. ................................ 128/325; 128/334 R; 227/DIG. 1
[58] Field of Search ................... 128/325, 326, 334 R, 128/335, 305; 227/DIG. 1

[56] References Cited

U.S. PATENT DOCUMENTS

| | | | |
|---|---|---|---|
| 2,968,041 | 1/1961 | Skold | 1/49.1 |
| 2,968,042 | 1/1961 | Yankee | 1/187 |
| 3,331,233 | 7/1967 | Ruskin | 72/410 |
| 3,665,924 | 5/1972 | Noiles et al. | 128/305 |
| 3,774,438 | 11/1973 | Weston | 72/410 |
| 3,899,914 | 8/1975 | Akiyama | 72/410 |
| 4,152,920 | 5/1979 | Green | 72/410 |
| 4,166,466 | 9/1979 | Jarvik | 128/325 |
| 4,226,242 | 10/1980 | Jarvik | 128/325 |
| 4,242,902 | 1/1981 | Green | 72/410 |
| 4,246,903 | 1/1981 | Larkin | 128/325 |
| 4,273,129 | 6/1981 | Boebel | 227/DIG. 1 |
| 4,296,751 | 10/1981 | Blake et al. | 128/325 |
| 4,316,468 | 2/1982 | Klieman et al. | 128/334 R |
| 4,325,376 | 4/1982 | Klieman et al. | 128/325 |

FOREIGN PATENT DOCUMENTS

| | | | |
|---|---|---|---|
| 1082552 | 7/1980 | Canada | 128/122 |
| 0000756 | 2/1979 | European Pat. Off. | |

Primary Examiner—Lee S. Cohen
Assistant Examiner—Steven Falk
Attorney, Agent, or Firm—John E. Nathan; Robert R. Jackson; Eugene S. Indyk

[57] ABSTRACT

Apparatus for applying surgical clips to tissue includes a self-contained supply of clips and is constructed to apply those clips, one at a time, through movement of the thumb and fingers of one hand. The clips are stored inside a sleeve along the length of the instrument, are fed into jaws at the distal end of the instrument, and are closed about tissue by a camming action produced by moving the jaws relative to the sleeve and camming them shut. An actuating and sequencing section controls feeding and clip deformation, and guarantees that the instrument is operated only in the proper sequence so as to avoid jamming.

35 Claims, 42 Drawing Figures

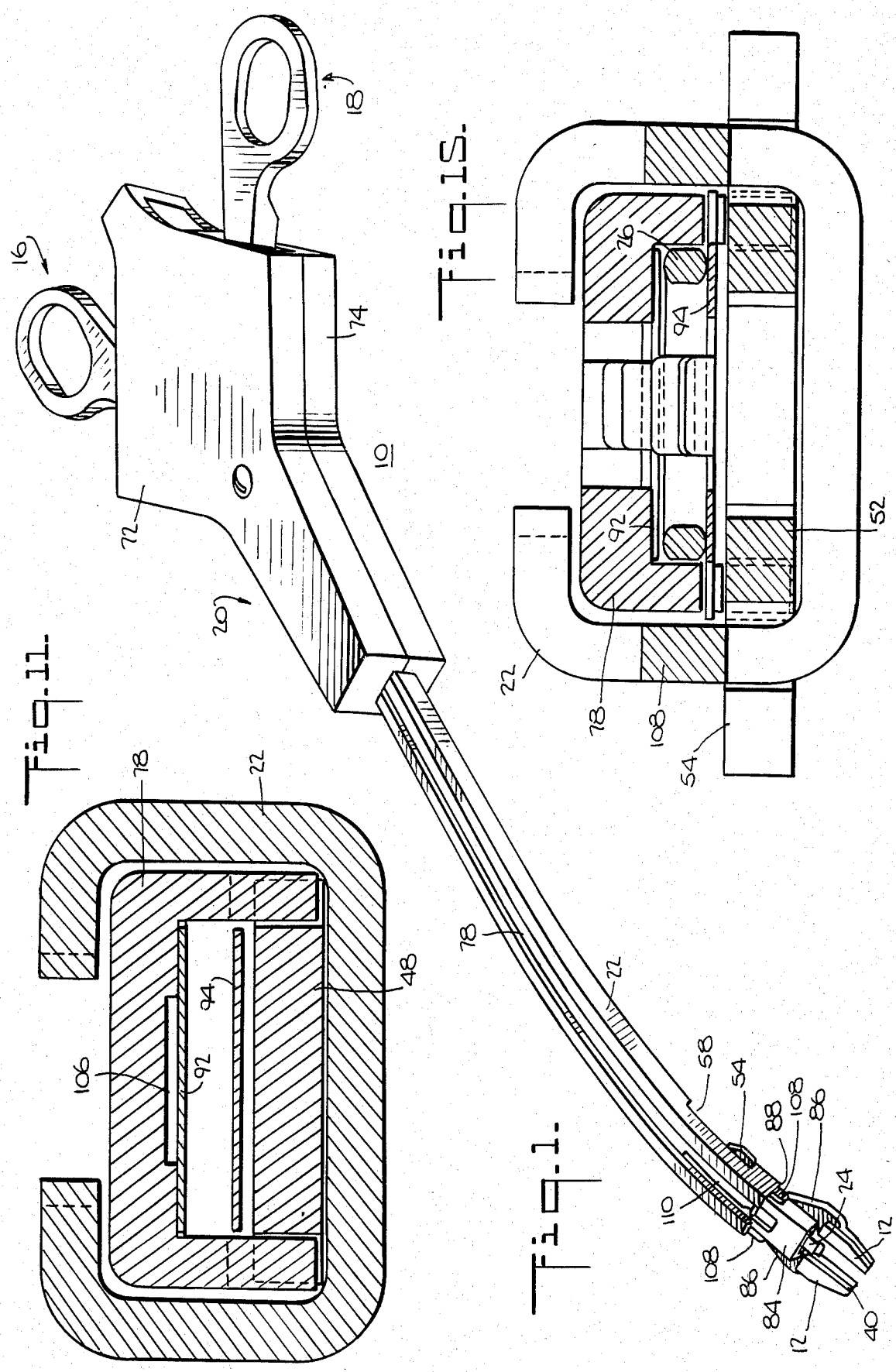

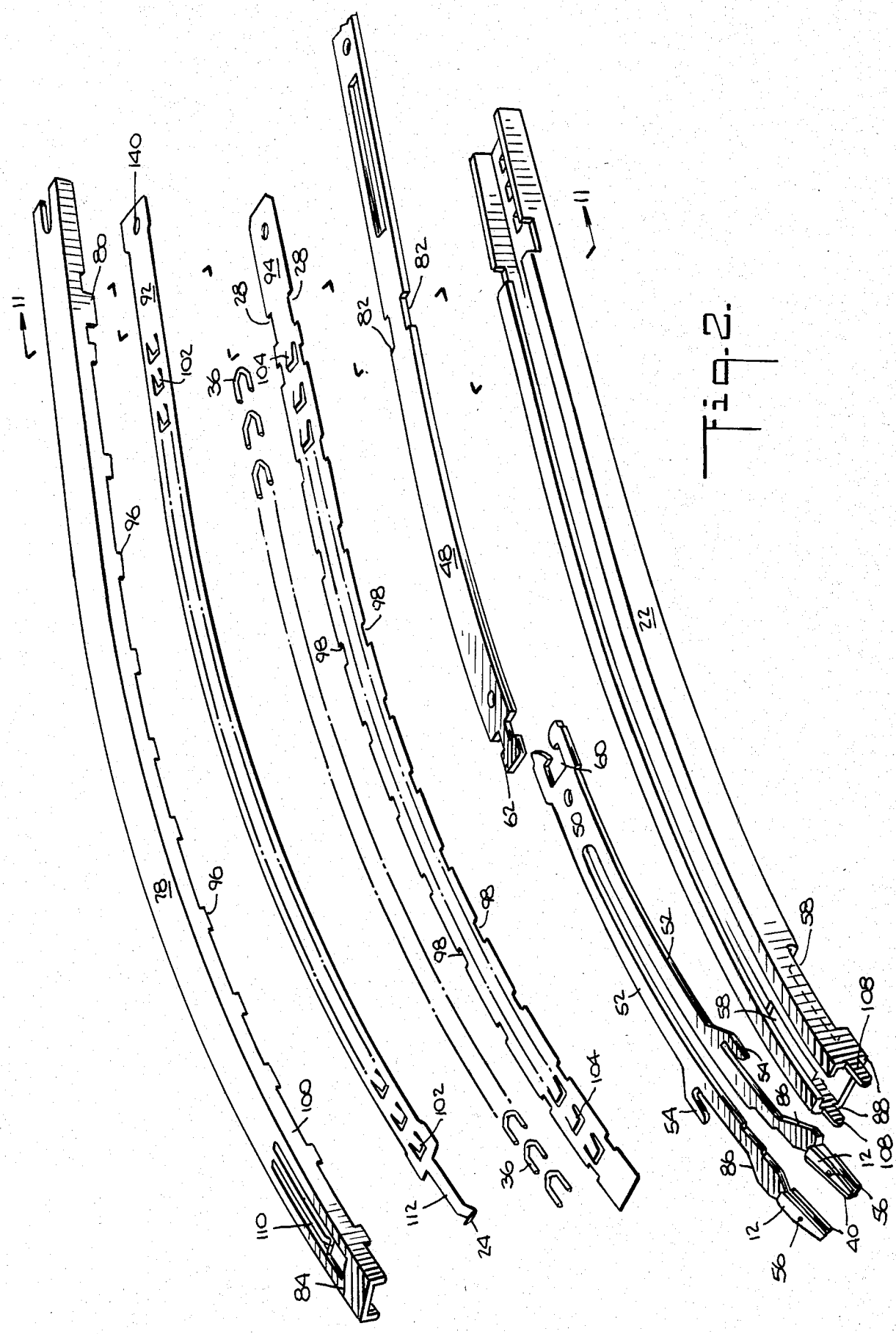

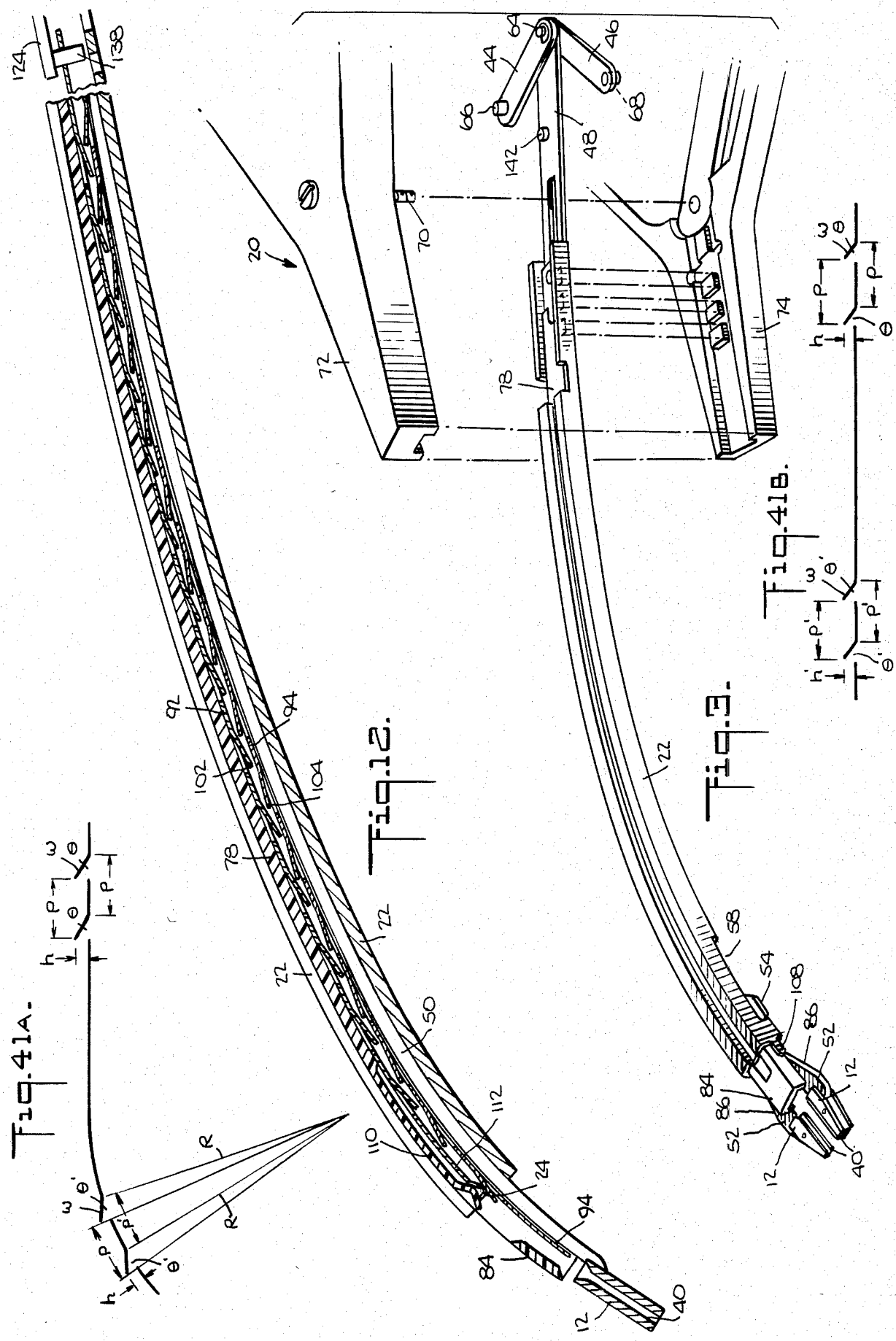

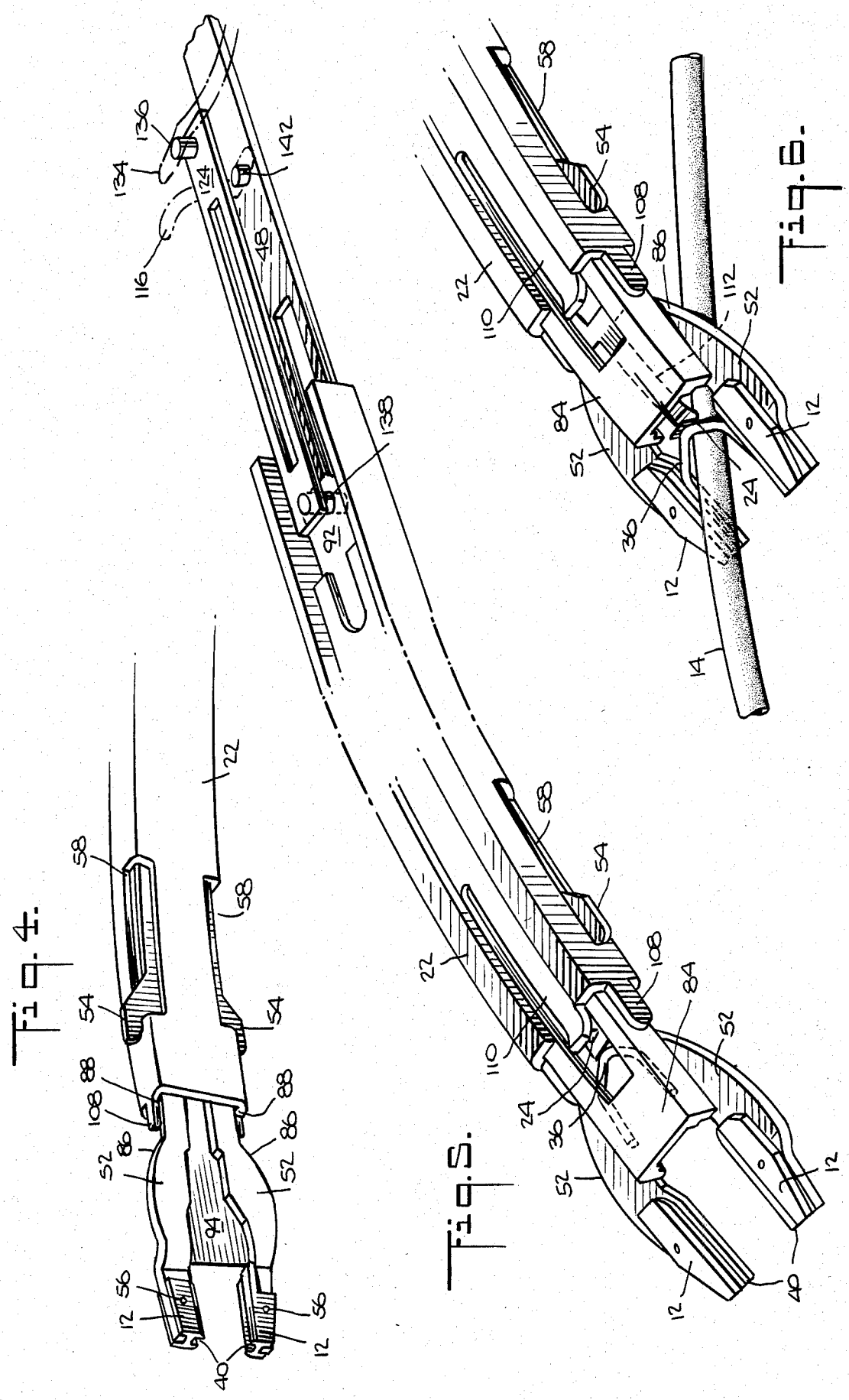

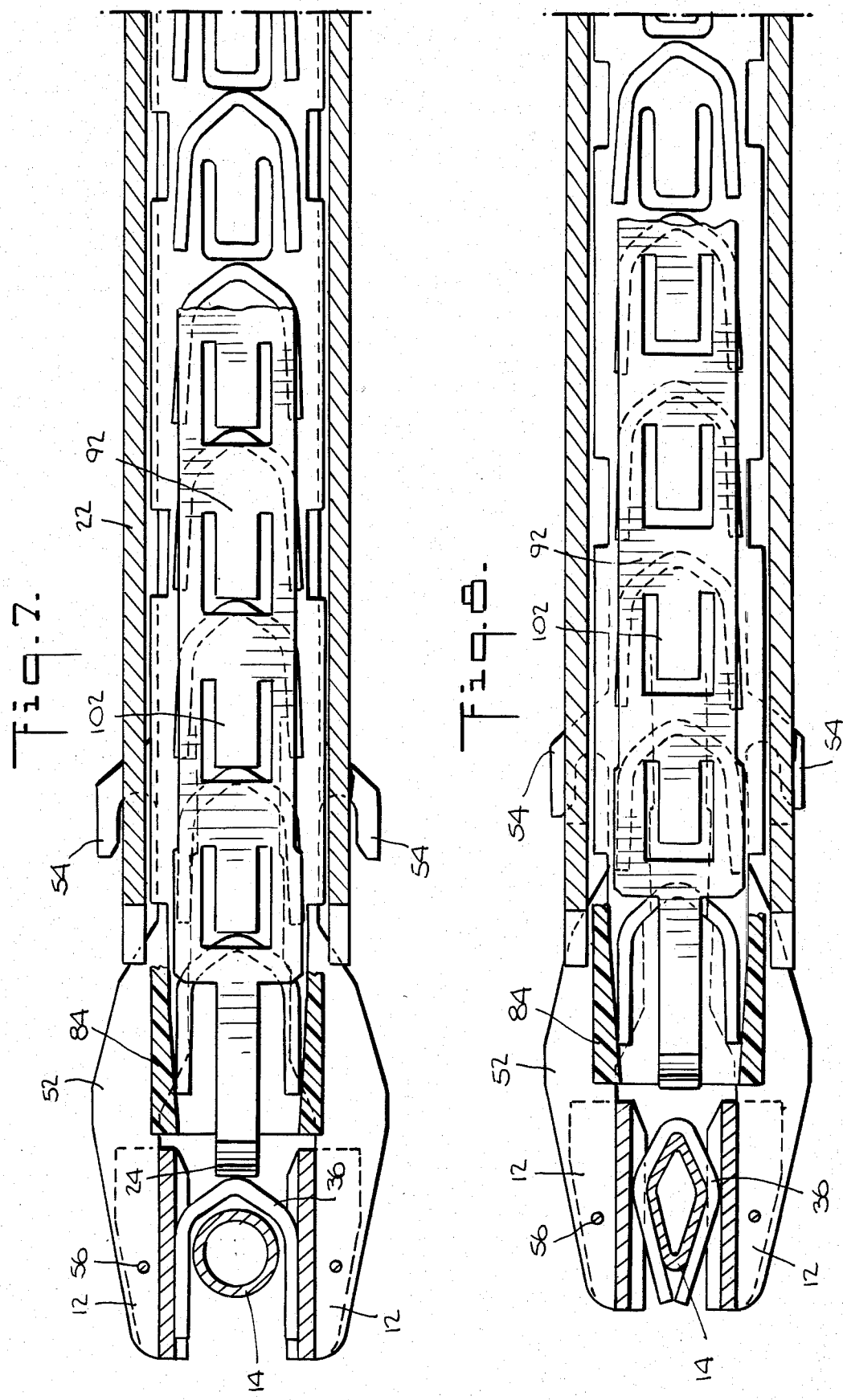

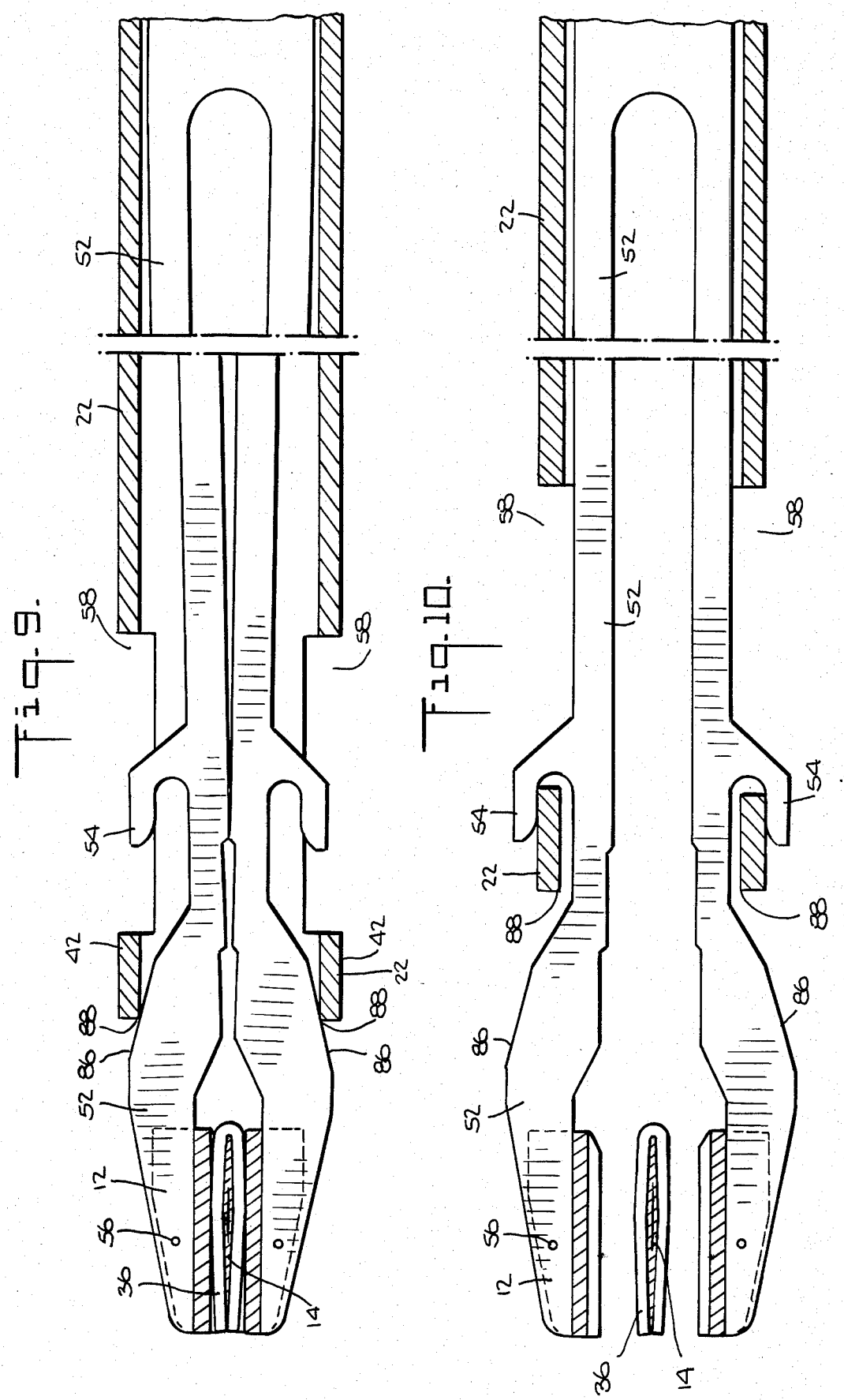

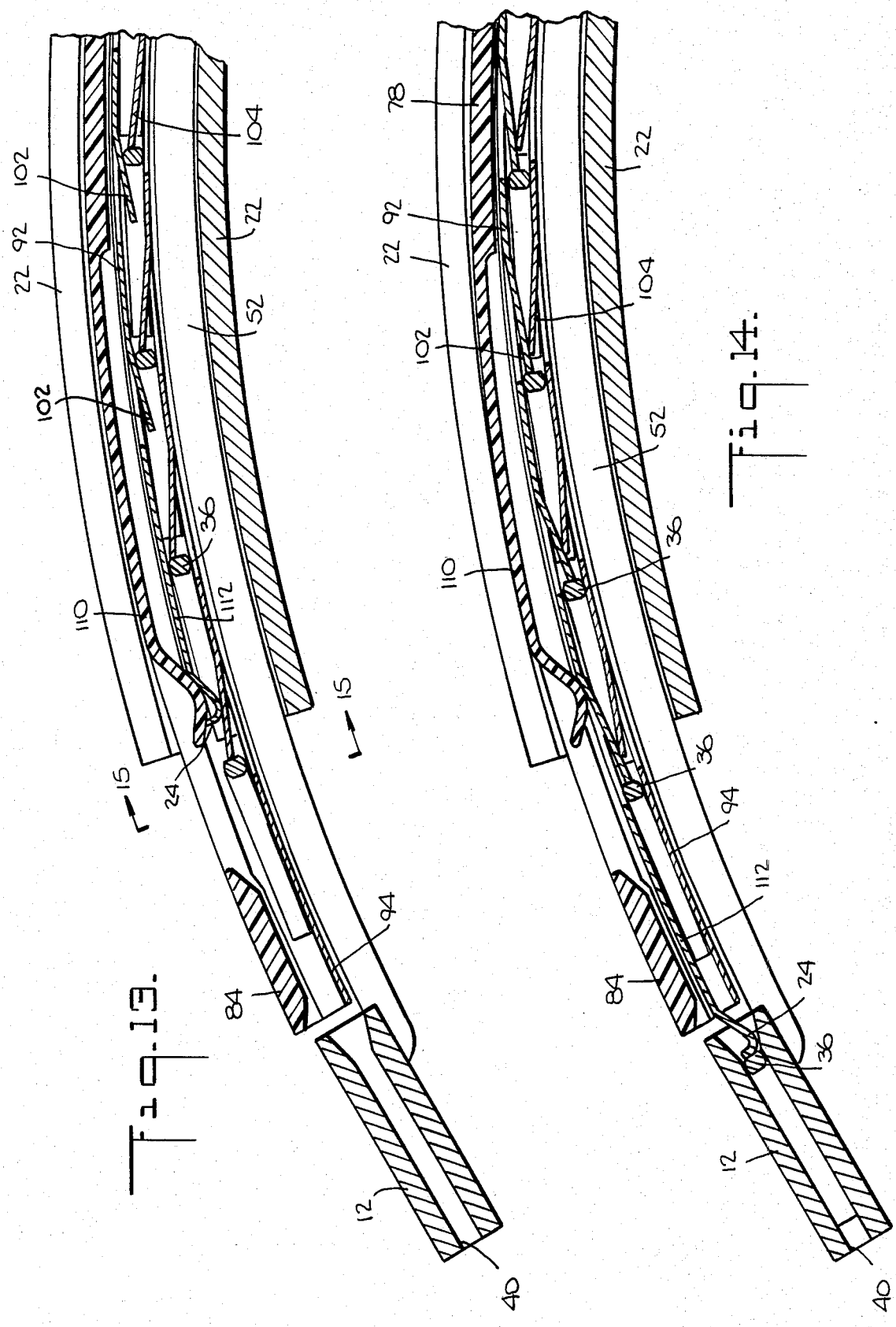

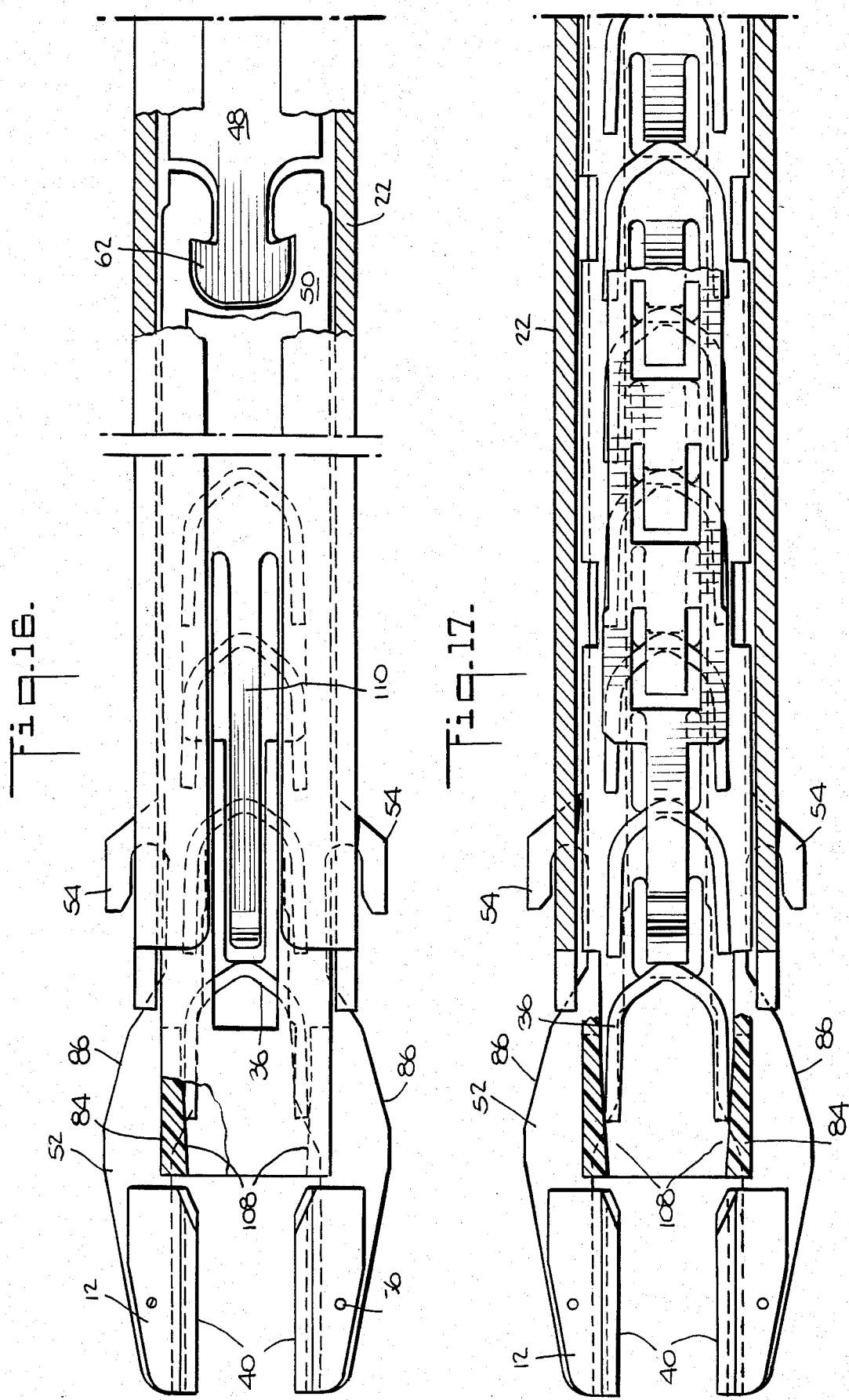

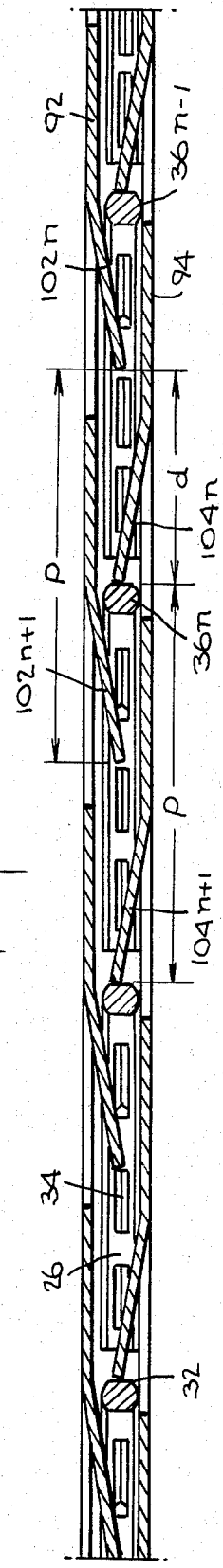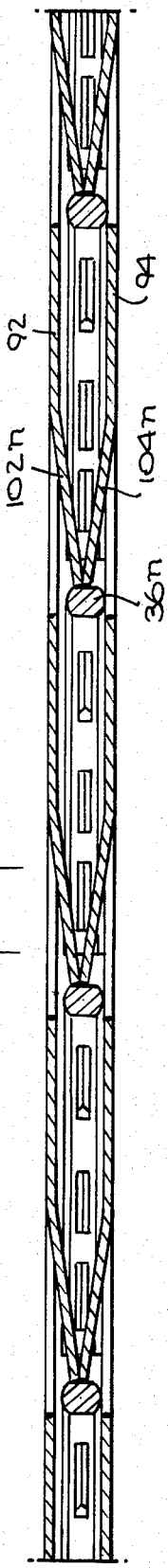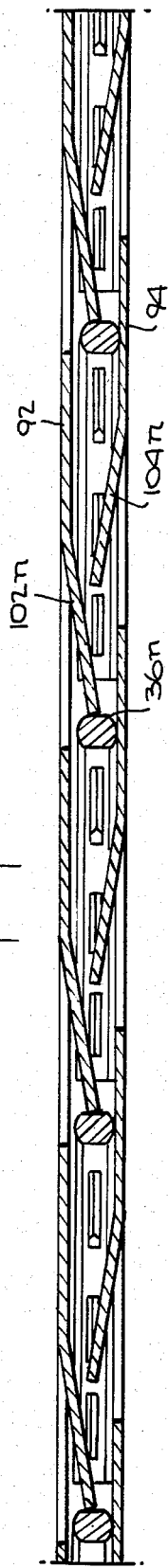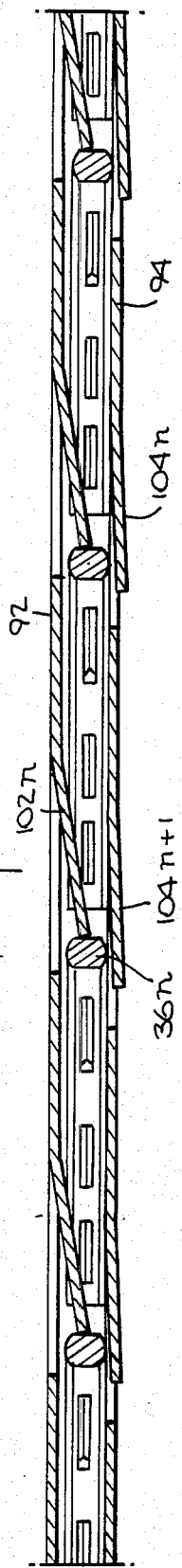

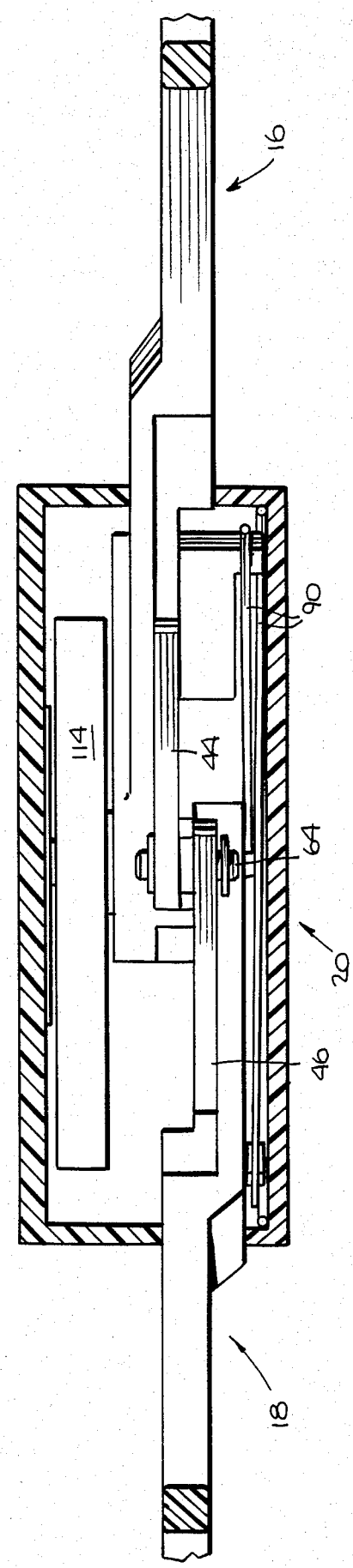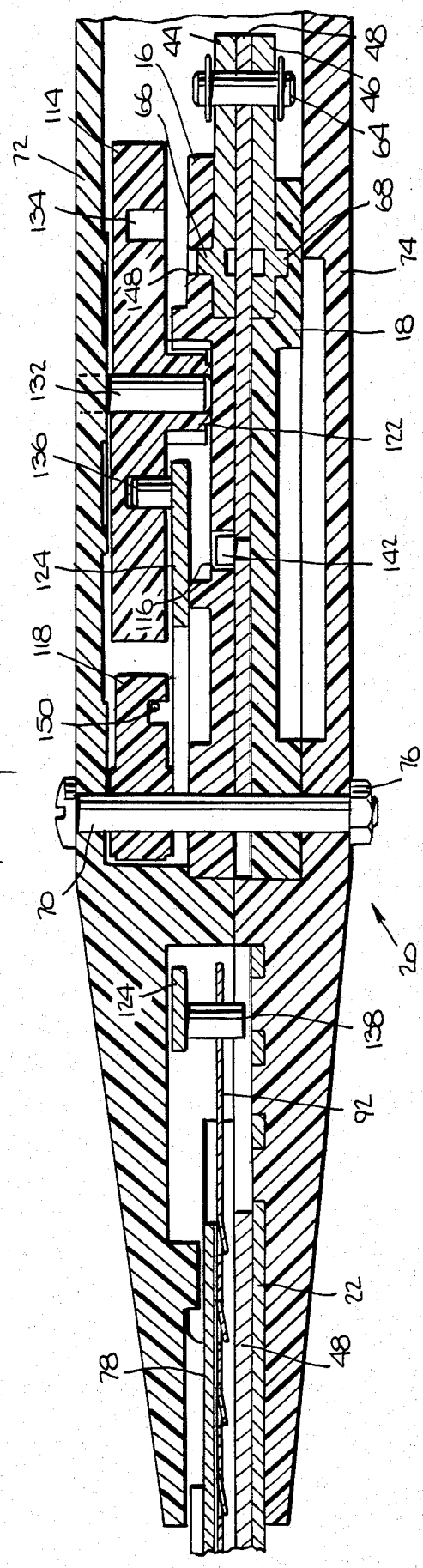

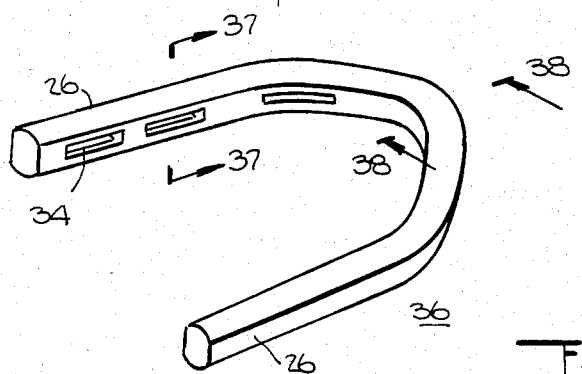
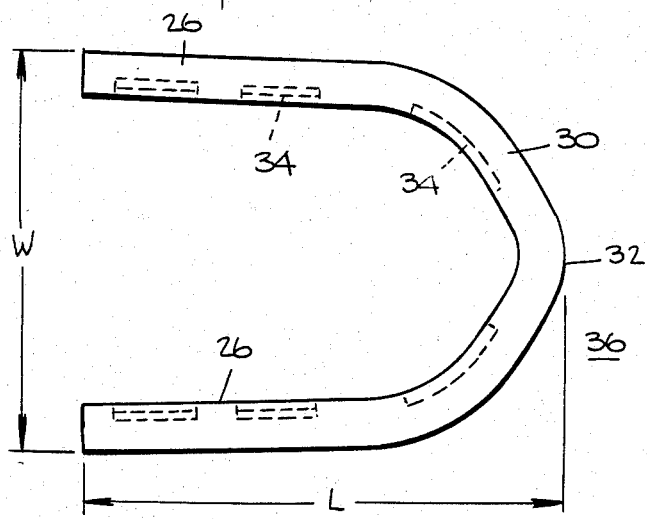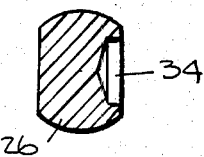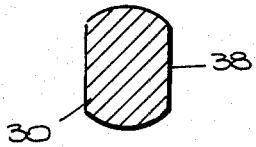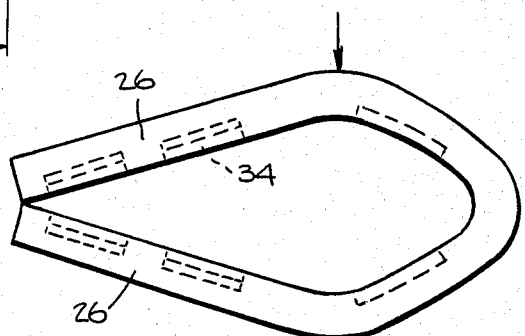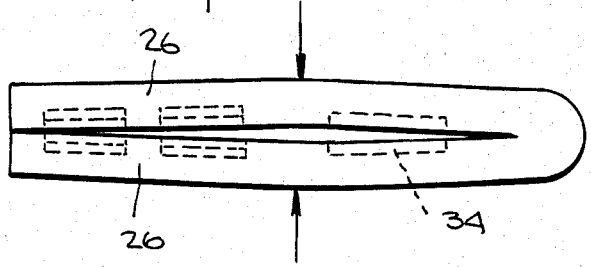

APPARATUS FOR APPLYING SURGICAL CLIPS

BACKGROUND OF THE INVENTION

1. Field of the Invention

This invention relates to apparatus for applying surgical clips to body tissue. More particularly, the invention relates to apparatus having a self-contained supply of surgical clips and constructed to apply those clips, one at a time, through relative movement of the thumb and fingers of one hand.

2. Description of the Prior Art

Surgical clips, also known as hemostatic clips, serve to seal or clamp off blood vessels or other sections of tissue which are cut during surgical procedures. Each clip has two coplanar arms which surround the tissue to be clamped. The clip applying instrument holds these arms while the clip is positioned about the tissue to be clamped and then brings the arms toward each other, in their common plane, to seal off the tissue.

A surgeon may apply twenty or more clips during the course of an operation. Early commercial instruments held one clip at a time, which a surgical assistant inserted in the instrument from a clip dispenser prior to each use. These instruments were generally of the scissor or plier variety in which the clip was held in jaws at the distal end of two pivoted lever arms. To handle the stresses encountered in closing the clip, these lever arms had to be of high beam strength. Use of high beam strength, surgical instrument grade materials increased the cost of these instruments so that they were sold as permanent instruments, and only the clip dispenser was disposable.

More recently, a disposable instrument, incorporating the clip dispenser as part of the instrument, has come into general use. This instrument is shown generally in U.S. Pat. Nos. 4,152,920 and 4,242,902, assigned to the assignee of this invention. It employs a movable clip cartridge mounted on the instrument. Clips are loaded into the jaws of the instrument through a pumping action in which the cartridge is slid forward and then backward over the jaws. As such, the instrument requires two hands to load a clip: one to move the cartridge and the other to hold the instrument. In many cases, this means that two people become involved in applying clips, as was the case with the separate dispenser instruments, since the surgeon's hand which is not holding the instrument, and thus theoretically could be used to move the cartridge, often is needed to hold the tissue being clamped in the proper orientation. On such occasions, the surgeon will present the instrument to an assistant, and the assistant will pump the cartridge to load a clip.

To close a clip, this instrument, rather than using pivoted levers, surrounds the jaws and their supporting arms with a sleeve and closes the jaws by moving them back into the sleeve and camming them shut through contact with the distal end of the sleeve. Because of the construction of the movable cartridge, this instrument is generally limited to the application of relatively small clips.

Instruments for applying surgical clips through the use of only one hand have also been developed. For example, U.S. Pat. No. 4,166,466, assigned to the assignee of this invention, shows a lever closure instrument in which part of the movement of the levers is used to feed a clip to the instrument's jaw and the remainder of the movement is used to close the clip. Canadian Pat. No. 1,082,552 and European Patent Publication No. A1 0,000,756 show other one-handed instruments. All of these instruments are of the lever closure type and thus require strong, expensive materials.

SUMMARY OF THE INVENTION

It is the object of this invention to produce an improved one-handed surgical clip applying instrument. In particular, the present invention provides a smaller, lighter, more versatile instrument by providing apparatus which can automatically sequence clip feeding and clip closure, and which can close the clip by movement of jaws into a sleeve, rather than by the pivoting of levers. By so doing, the invention allows the use of larger clips without producing an unwieldy instrument, as well as the use of less expensive materials of lower strength and smaller dimensions, so that the whole instrument economically can be made completely disposable. Other features of this invention will be apparent from the detailed disclosure which follows.

BRIEF DESCRIPTION OF THE DRAWINGS

FIG. 1 is an overall perspective view of an illustrative embodiment of the surgical clip applying apparatus of this invention.

FIG. 2 is a perspective, exploded view of the distal part of the clip deforming and the clip storing and advancing sections of the instrument.

FIG. 3 is a perspective view, partially exploded, showing the connection of the instrument sleeve to the upper and lower portions of the instrument housing.

FIG. 4 is a perspective view from underneath of the distal portion of the instrument's sleeve and the jaws.

FIG. 5 is a composite, perspective view of selected components of the clip deforming, clip storing and advancing, and actuating and sequencing sections, showing certain of the interconnections between those sections.

FIG. 6 is a perspective view of the distal portion of the instrument showing placement of a clip about tissue to be clamped.

FIGS. 7 through 10 are plan cross-sectional views showing clip deformation, beginning with placement of a clip about the tissue to be clamped (FIG. 7), followed by intermediate deformation (FIG. 8), complete deformation (FIG. 9) and jaw release and resetting of the instrument (FIG. 10).

FIG. 11 is a transverse cross-sectional view, along line 11—11 in FIG. 2, showing the assembled relationship of the components of the clip storing and advancing section.

FIG. 12 is a medial longitudinal cross-sectional view through the instrument sleeve showing the arrangement of the clip storing and advancing section of the instrument within the sleeve. The clips have been omitted for clarity.

FIGS. 13 and 14 are enlarged medial longitudinal cross-sectional views of the distal portion of the instrument prior to and after clip advancement, respectively.

FIG. 15 is a transverse cross-sectional view of the distal portion of the instrument taken along line 15—15 in FIG. 13.

FIG. 16 is an enlarged plan view, partially in section, of the clip storing, advancing, and deforming sections of the instrument.

FIG. 17 is an enlarged plan cross-sectional view of the distal portion of the clip storing, advancing, and deforming sections of the instrument.

FIGS. 18 through 25 are medial longitudinal cross-sectional views showing the movement of a representative clip through the clip storing and advancing section during feeding and resetting.

FIG. 28 is an end view, partially in transverse section, of the actuating and sequencing section of the instrument.

FIG. 29 is a medial longitudinal cross-sectional view of the actuating and sequencing section of the instrument.

FIG. 35 is a perspective view of a typical surgical clip applied by the instrument.

FIG. 36 is a plan view of the surgical clip of FIG. 35.

FIGS. 37 and 38 are sectional views of the surgical clip of FIG. 35 taken along lines 37—37 and 38—38, respectively.

FIG. 39 is a plan view showing a partially deformed clip.

FIG. 40 is a plan view showing a completely deformed clip.

FIG. 41a is a schematic diagram of a convexly curved, toothed ratchet, showing the differences in spacing and sizing of teeth in the flat and curved portions of the ratchet. FIG. 41b shows the same ratchet prior to being flexed into the curved path. Distances and angles have been exaggerated in both figures for purposes of illustration.

DESCRIPTION OF THE PREFERRED EMBODIMENT

Figure 22:
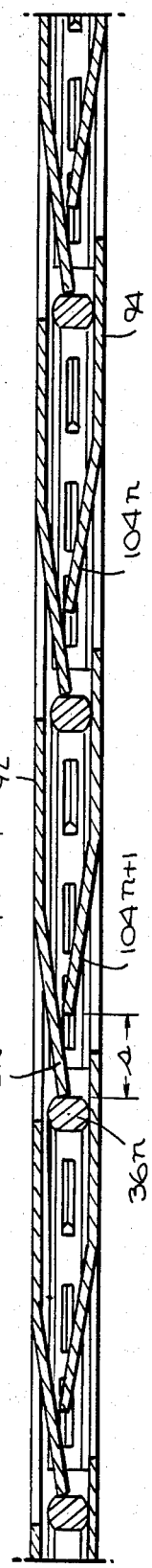

The one-handed clip applying apparatus 10 of this invention is shown generally in FIG. 1. At its distal end, the apparatus has jaws 12 for receiving, holding and deforming a surgical clip. At its proximal end are spring-loaded ring handles 16 and 18, which the surgeon engages with the thumb and fingers of one hand.

Between the jaws 12 and the handles 16, 18 is the body of the instrument, consisting of housing 20 and longitudinally curved sleeve 22. Housing 20 contains the actuating and sequencing mechanism which responds to the movement of the handles to feed and close a clip, and then resets for application of the next clip. Inside curved sleeve 22 are approximately twenty clips stored flat, one behind the other. By arranging the instrument in this manner, that is, by curving sleeve 22, storing the clips flat inside the sleeve and locating the operating mechanism inside housing 20 near the proximal end of the instrument, the surgeon has an essentially unobstructed view of jaws 12. This allows him easily and accurately to position the clip about the tissue to be sealed off.

To operate the instrument, the surgeon moves ring handles 16 and 18 towards each other. The first part of the motion, consisting of inward movement of handle 16 with handle 18 remaining stationary, feeds the forwardmost clip to jaws 12, as well as indexing the supply of clips in sleeve 22 one step forward. A clutch, discussed below, holds the instrument in this intermediate position allowing the surgeon to place the clip 36 about the tissue 14 to be clamped (FIG. 6). Clip stop 24, which is also used to push forwardmost clip 36 into jaws 12, remains behind the clip during this stage so as to prevent the clip from being pushed back into the instrument as it comes into contact with tissue.

Once clip 36 is properly positioned, the surgeon moves ring handles 16, 18 further together, both handles moving inward, to close clip 36 about the tissue. This inward movement of handles 16, 18 also retracts clip stop 24 somewhat to accommodate the rearward movement of the apex of the clip which occurs as the clip is closed. Upon release of handles 16, 18, the instrument resets so that it is ready to apply the next clip. The process is repeated until the clip supply is exhausted, after which the instrument is disposed of.

The structure of a typical surgical or hemostatic clip 36 for use with the instrument is shown in FIGS. 35 through 38. Clip 36 includes arms 26, which are slightly sprung outward, and a crown portion 30 having an apex 32. The inner surface of arms 26 and crown 30 can be grooved as shown at 34 to grasp the tissue more securely. As discussed above, the present invention permits the use of clips of varying sizes, including clips of relatively large size. Thus, clips having overall lengths (L in FIG. 36) on the order of approximately 8 mm and corresponding widths (W in FIG. 36) on the order of approximately 7 mm are easily carried in and applied by the instrument without it becoming unduly large or expensive. Larger and smaller clips also can be applied.

The detailed operation of the instrument is best understood in terms of three sections: a clip deforming section, a clip storing and advancing section, and an actuating and sequencing section. In terms of these sections, the instrument, under the control of the actuating and sequencing section, feeds one surgical clip at a time from the clip storing and advancing section to the clip deforming section, deforms that clip and then resets for repetition of the cycle.

The components of the clip deforming section are shown in FIGS. 2 through 10. The operative portion of this section is jaws 12, at the distal end of the instrument, which receive a clip fed from the clip storing and advancing section, hold the clip while it is placed around the tissue to be clamped and then deform the clip to seal the tissue by moving the clip arms inward towards each other. Jaws 12 include grooves 40 which securely hold the clip while it is being placed about the tissue and while it is being deformed.

Jaws 12 are connected to handles 16 and 18, which provide the motive power for closing a clip, through links 44 and 46 (FIG. 3), jaw blade extension 48 (FIGS. 2 and 3) and curved, bifurcated jaw blade 50 (FIG. 2). Jaw blade 50 has spaced-apart arms 52 which flex towards each other during clip closure. Pins 56 connect jaws 12 to jaw blade 50; interlocking elements 60 and 62 interconnect jaw blade 50 and jaw blade extension 48; pin 64 (FIG. 3) connects one end of each link 44, 46 to jaw blade extension 48; and pins 66 and 68 (FIGS. 3 and 31) connect the other ends of links 44, 46 to handles 16, 18. Handles 16, 18 pivot about shaft 70 (FIG. 3), which passes through the upper and lower portions 72 and 74 of instrument housing 20, and which holds those portions together by, for example, nut 76 engaging threads on one end of the shaft (see FIG. 29).

Jaw blade 50 and jaw blade extension 48 ride within curved sleeve 22 which extends from and is rigidly attached to housing 20 (see FIG. 3). Attached to jaw blade extension 48 is clip carrier housing 78 (FIG. 2). The attachment is made through feet 80 which depend from housing 78 and mate with slots 82 in extension 48. Clip carrier housing 78, jaw blade 50 and jaw blade extension 48 are sized to fit closely within sleeve 22. The distal portion 84 of clip carrier housing 78 sits directly behind jaws 12 to insure reliable feeding of clips into the jaws.

Figure 33:
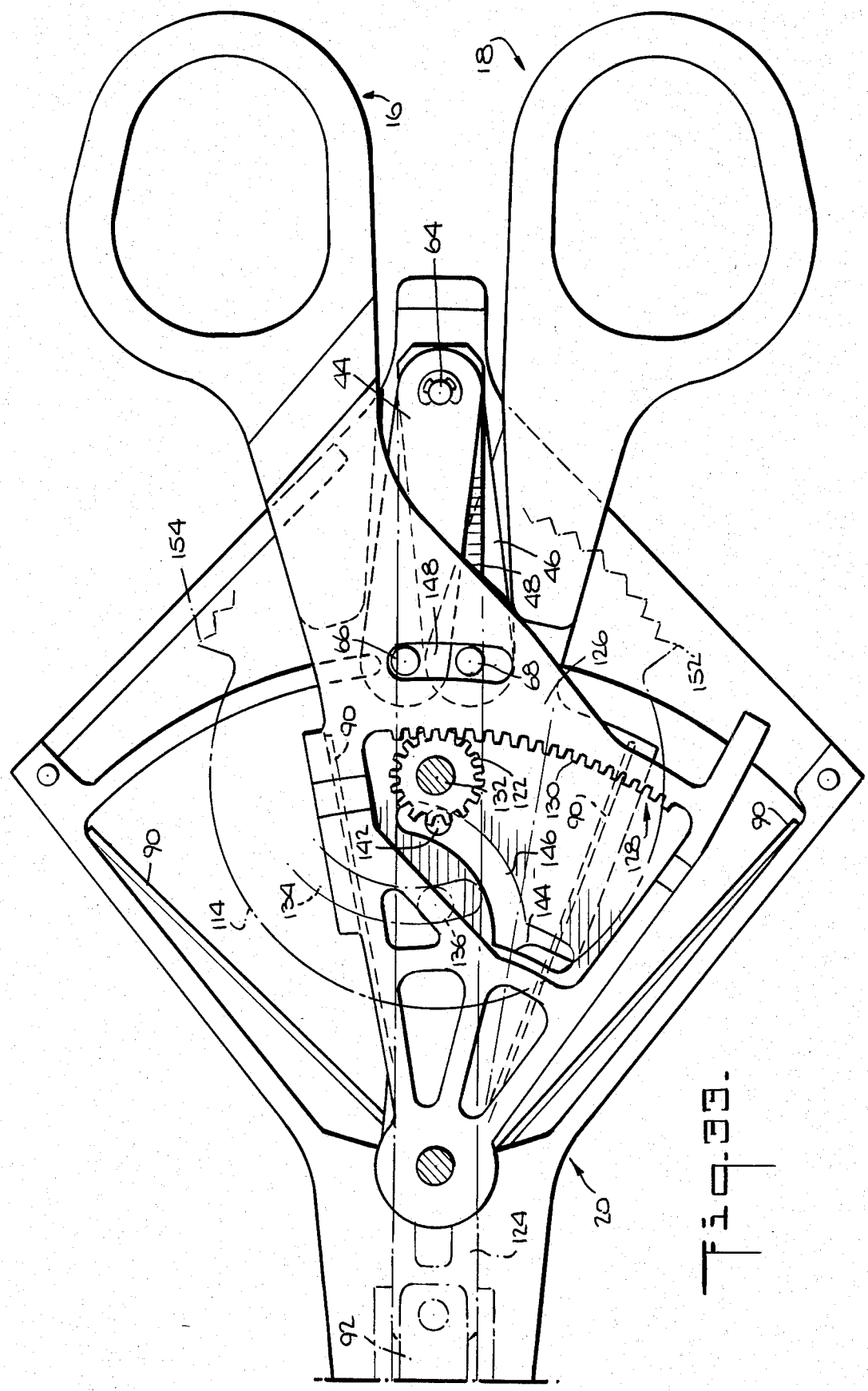

Operation of the clip deforming section proceeds as follows. As the surgeon moves handles 16 and 18 inward, links 44 and 46 cause jaw blade extension 48 and jaw blade 50, as well as clip carrier housing 78, to move proximally, bringing cam surface 86 on each jaw blade arm 52 into contact with an associated cam surface 88 on sleeve 22. Further proximal movement of jaw blade 50 forces jaws 12 toward each other in their common plane, deforming the clip. Note that clip carrier housing 78, because it is attached to and moves with jaw blade extension 48, automatically moves out of the way of the closing jaws. Upon the completion of clamping, the surgeon releases handles 16, 18, which move outward through the force of springs 90 (see for example FIG. 33 and discussion below), causing jaw blade extension 48, jaw blade 50 and clip carrier housing 78 to move distally to their initial, resting positions. To hold jaws 12 in vertical alignment during their proximal and distal movement, sleeve 22 includes, at its distal end, projections 108 which constrain the jaws from moving away from the bottom surface of the sleeve. 7

The deformation of a typical clip 36 is depicted in FIGS. 36, 39 and 40, where FIG. 36 shows an undeformed clip, FIG. 39 a partially deformed clip and FIG. 40 the final configuration (see also FIGS. 7 through 10). Note that the clip arms touch first at their tips to enclose the tissue and then the rest of the clip moves inward to seal the tissue.

Bifurcated jaw blade 50, in addition to flexing inward during clip closure, is constructed to hold securely a surgical clip during placement about the tissue to be clamped. Specifically, arms 52 of jaw blade 50 are biased inward to provide automatically inward pressure on arms 26 of the clip to hold it securely. To establish an initial, spaced-apart position for jaws 12, appropriate for reliable feeding, arms 52 are provided with projections 54, which extend through and forward of slots 58 in sleeve 22 (see for example FIGS. 9 and 10). In these positions, projections 54 can contact the outer surface of sleeve 22 at surfaces 42 and establish a fixed distance to which the inward biasing of jaw blade 50 can bring jaws 12 in the resting state. This arrangement does not interfere with closing of the clip, because as jaw blade 50 moves proximally, projections 54 move back from surfaces 42 and are free to move into and through slots 58 as jaws 12 are cammed inward by the contact of cam surface 86 on each jaw blade arm 52 with cam surface 88 on sleeve 22. This construction of jaw blade 50 provides a source of inward pressure on the clip which, because it is not dependent upon the precise location of jaws 12 relative to the distal end of sleeve 22, is relatively insensitive to manufacturing tolerances.

The components of the clip storing and advancing section are shown in an exploded view in FIG. 2. The section has four basic parts: clip carrier housing 78, feed ratchet 92, backstop ratchet 94 and the surgical clips 36. As shown in FIGS. 11 through 15, feed ratchet 92, backstop ratchet 94 and surgical clips 36 fit inside clip carrier housing 78. Backstop ratchet 94 is attached to the bottom of the clip carrier housing 78 by means of feet 80 and 96 which depend from housing 78 (see FIG. 2). Feet 96 mate with and are fastened to slots 98 in ratchet 94; feet 80 engage slots 28 in ratchet 94 and are fastened to slots 82 in jaw blade extension 48. Feet 96 extend beyond the plane of the bottom of backstop ratchet 94 and rest on either jaw blade 50 or jaw blade extension 48, depending on the location of a particular foot, so as to leave a space between the bottom of backstop ratchet 94 and the top of jaw blade 50 or jaw blade extension 48. Feed ratchet 92 rides above backstop ratchet 94, the spacing between the inner surfaces of these ratchets being essentially equal to the thickness of a clip 36 so that the clips are held between the two ratchets. The walls 100 of clip carrier housing 78 similarly are spaced apart by a distance essentially equal to the width W of a clip 36 so as to confine the clip and define its course of motion.

Clip carrier housing 78, feed ratchet 92, and backstop ratchet 94 are each longitudinally flexible to conform to and to pass around the forward curved portion of sleeve 22. As discussed above, clip carrier housing 78 and its contents fit inside curved sleeve 22 with the distal end 84 of clip carrier housing 78 directly behind jaws 12.

As shown in FIG. 2, both the feed and backstop ratchets 92, 94 have a series of forward facing teeth 102 and 104, respectively. Feed ratchet 92 has at least one tooth for each clip 36 supplied with the instrument, e.g., at least twenty teeth if the instrument is to apply twenty clips. Backstop ratchet 94, on the other hand, can have one less tooth than the number of clips because the last clip in the unit does not require a backstop tooth.

Teeth 102 and 104 are stamped out of the ratchet body and behave as leaf springs which flex when they come in contact with teeth on the other ratchet or pass over a clip during the feeding and resetting cycle. The space left between the bottom of backstop ratchet 94 and the top of jaw blade 50 and jaw blade extention 48 by feet 96, as well as groove 106 in the top of clip carrier housing 78 (FIG. 11), provide relief spaces for the teeth to flex into when they are in the process of passing over a clip.

Teeth 102 and 104 are designed to contact the clips at or slightly beyond half the thickness of the clip wire. Note that the outward facing surface of the clip wire is flat at these locations (see FIG. 38 at 38) to insure positive engagement between the ratchet teeth and the clip and to help prevent the teeth from sliding over the clips. Also, the teeth are distributed along the ratchet so that the clips are spaced apart by the nominal pitch space distance p. Because part of each of the ratchets 92 and 94 lie in the curved portion of sleeve 22, the height to which the teeth project from the ratchet when the ratchet is flat and the spacing between the tips or clip engaging portions of the teeth when the ratchet is flat must vary between the curved and flat portions of the ratchet. Specifically, the forwardmost five or so teeth 104 of backstop ratchet 94 are made slightly lower and their tips slightly closer together, and the forwardmost five or so teeth 102 of feed ratchet 92 are made slightly higher and their tips slightly farther apart, when the ratchets are flat, than the heights and tip spacings of ratchet teeth located in the flat part of sleeve 22. These changes accommodate for the convex (tooth side) curvature of backstop ratchet 94 and the concave (tooth side) curvature of feed ratchet 92 in the curved region, which otherwise would cause the teeth either to extend out too much or too little into the path of the clips and would cause the tips of the teeth, and thus the clips, either to be too far apart or too close together.

These changes are illustrated schematically in FIGS. 41a and 41b for a convex (tooth side) curved ratchet (e.g. backstop ratchet 94) where the change in tooth height is achieved by varying the angle ($\theta$) to which the teeth are bent away from the body of the ratchet. By comparing FIGS. 41a and 41b, it can be seen that by making p' less than p and by making $\theta'$ less than $\theta$, which makes h' less than h, the spacing between the tips of the teeth when the ratchet is curved is held constant at the desired value p and the height of the tips of the teeth above the body of the ratchet is held constant at the desired value h. The relationships between the parameters $\theta$, $\theta'$, p, p', h, h', w (the length of a tooth) and R (the radius of curvature at the level of the body of the ratchet) can be written:

$$h = w \sin \theta,$$

$$h' = w \sin \theta',$$

$$p/(R+h) = p'/R,$$

and $$(h+R)^2 = w^2 + R^2 - 2wR \cos(90° + \theta'),$$

from which p', $\theta'$, and h' can be calculated. Similar geometric relationships hold for a concave (tooth side) curved ratchet (e.g. feed ratchet 92). In this case, p' is greater than p, and $\theta'$ is greater than $\theta$.

The feeding of clips occurs through movement of feed ratchet 92 with respect to backstop ratchet 94. Under the control of the actuating and sequencing section (discussed below), feed ratchet 92 traverses a distal-proximal cycle relative to backstop ratchet 94. The distal motion moves the leading clip into jaws 12 and indexes each of the clips remaining in the instrument one tooth on backstop ratchet 94 closer to jaws 12. The proximal motion resets the mechanism for the next feed. Because backstop ratchet 94, through its attachment to clip carrier housing 78 and thus jaw blade extension 48, moves proximally and then distally as jaws 12 close and then open, feed ratchet 92, as seen from such stationary elements as instrument housing 20 or sleeve 22, actually traverses a distal-proximal-distal-proximal cycle as handles 16 and 18 move from their outermost position through their innermost position and back to their outermost position. However, as discussed below in connection with the actuating and sequencing section, because feed ratchet 92 in essence moves synchronously with backstop ratchet 94, when the latter is in motion, in terms of the feeding process, the intermediate proximal-distal cycle of feed ratchet 92 which tracks the motion of backstop ratchet 94 can be ignored. Accordingly, the description of feeding which follows is in terms of the relative motion of the backstop and feed ratchets, not their absolute motion with respect to stationary instrument housing 20 and sleeve 22.

FIGS. 18 through 25 show movement of a representative clip 36n.

FIG. 18 shows the resting or initial condition. The apex of clip 36n is touching or just in front of the forward edge of tooth 104n of backstop ratchet 94. Tooth 102n of feed ratchet 92 is a distance d behind tooth 104n of backstop ratchet 94. The tips of adjacent teeth of both ratchets are spaced apart by the nominal pitch space distance p.

FIGS. 19 to 25 show feeding of the clip. In FIG. 19, feed ratchet tooth 102n has moved forward (distally) to contact backstop ratchet tooth 104n, has flexed that tooth (and has been flexed itself) and is now in contact with the apex 32 of clip 36n. In FIG. 20, feed ratchet tooth 102n has moved forward from the location of backstop tooth 104n, carrying clip 36n with it. As this continues, clip 36n and its feed tooth 102n meet and ride over the next forward backstop tooth 104n+1 (FIG. 21). Forward feeding continues until clip 36n and feed tooth 102n have completely cleared the backstop tooth 104n+1 and have gone beyond that tooth by a distance s (FIG. 22). Note that the feed tooth 102n has completely passed two backstop teeth 104n and 104n+1.

Figure 23:
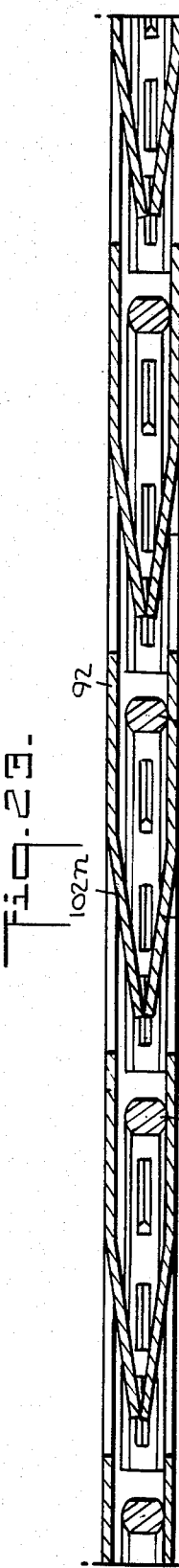
Figure 24:
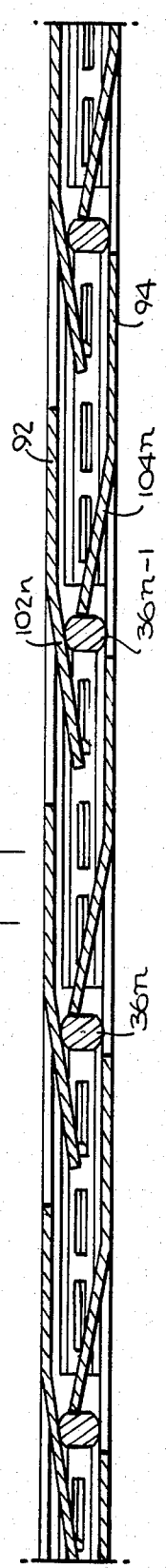
Figure 25:
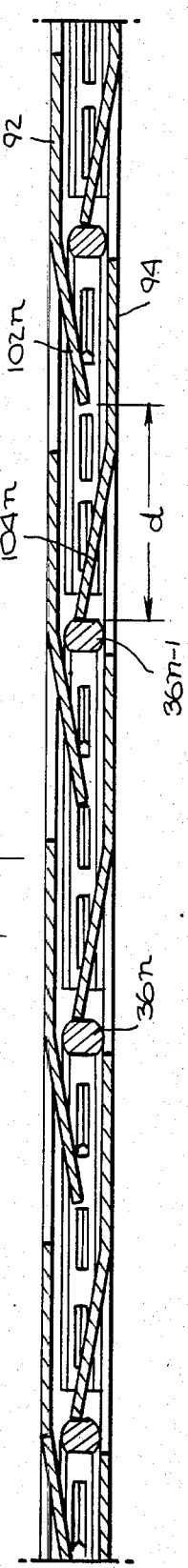

Feed ratchet 92 now begins its return to the resting state. First feed tooth 102n, leaving behind clip 36n, contacts backstop tooth 104n+1 and they both flex as the feed tooth passes over the backstop tooth (FIG. 23). Next, feed tooth 102n meets clip 36n−1 and pulls it back against backstop tooth 104n (FIG. 24). Then, as backstop tooth 104n holds clip 36n−1, feed tooth 102n flexes and passes over the clip and then over backstop tooth 104n. Finally, feed tooth 102n comes to rest in its initial position, a distance d behind the backstop tooth 104n (FIG. 25).

As discussed in more detail below in connection with the description of the actuating and sequencing section, the return movement of feed ratchet 92 is actually preceeded by a short return stroke (less than the distance which would place feed tooth 102n behind clip 36n−1) which occurs at the time of the initial closing movement of the jaws and serves to move the forwardmost feed tooth 24 (FIG. 1) proximally to accommodate the proximal movement of the apex of the clip as the clip is closed by the closing jaws. This short proximal stroke is retraced when the handles are released and is followed by the full return stroke.

The distances d and s—the overstroke distances—are provided to insure reliable feeding in view of the manufacturing tolerances of the parts involved. As long as the total length of the stroke (d+p+s) is less than 2×p, the clips will be moved forward a net distance of only p for each cycle of the feed ratchet.

The motion of the forwardmost or clip stop tooth 24 is similar to that of the other feed ratchet teeth 102 except that rather than pushing its associated clip past the next forward backstop tooth 104, tooth 24 pushes its clip into jaws 12. To guide the forwardmost clip into jaws 12, the forward part of clip carrier housing 78 includes ramps 108 (FIG. 17) which bring the clip arms into contact with jaw grooves 40. Clip carrier housing 78 also includes spring element 110 (FIG. 13) which rides against the shank 112 of clip stop tooth 24 to cause that tooth to follow the curve of sleeve 22 and jaw blade arms 52.

The spacing between clip stop tooth 24 and the tooth 102 just behind it is slightly greater than the pitch space distance p. This allows clip stop tooth 24 to extend further into jaws 12 so as to facilitate clip feeding. The difference in spacing is less than the overstroke distance d so that during the reset cycle, the forwardmost tooth 24 comes to rest behind the forwardmost clip, although at a location somewhat closer to this clip than the spacing d which separates the remaining teeth 102 on feed ratchet 92 from the clips they are about to feed. Because of this difference in location of clip stop tooth 24, the forwardmost clip is contacted and begins to move slightly before the other clips, and it moves slightly farther.

The actuating and sequencing section of the instrument is shown in FIGS. 26 through 34. This section coordinates the functions of (1) clip feeding, (2) clip closing and (3) instrument reset, as well as insuring that the instrument is not operated out of its proper sequence. The basic components of the actuating and sequencing section are handles 16 and 18 which receive the inward motive power from the surgeon for feeding and closing a clip; rotatable cam 114, which controls the movement of feed ratchet 92; sequencing slot 116 in handle 16, which controls the clip deforming section; pawl 118 (FIG. 27) which, with teeth 120 on rotatable cam 114, serves as a two-way clutch to insure that each step in the feeding-clamping-resetting cycle is completed before the next step is begun; and springs 90 (FIG. 26) which provide the outward motive power needed to reset the instrument. A detailed discussion of how these various elements produce the feeding-closing-resetting cycle follows.

Figure 31:
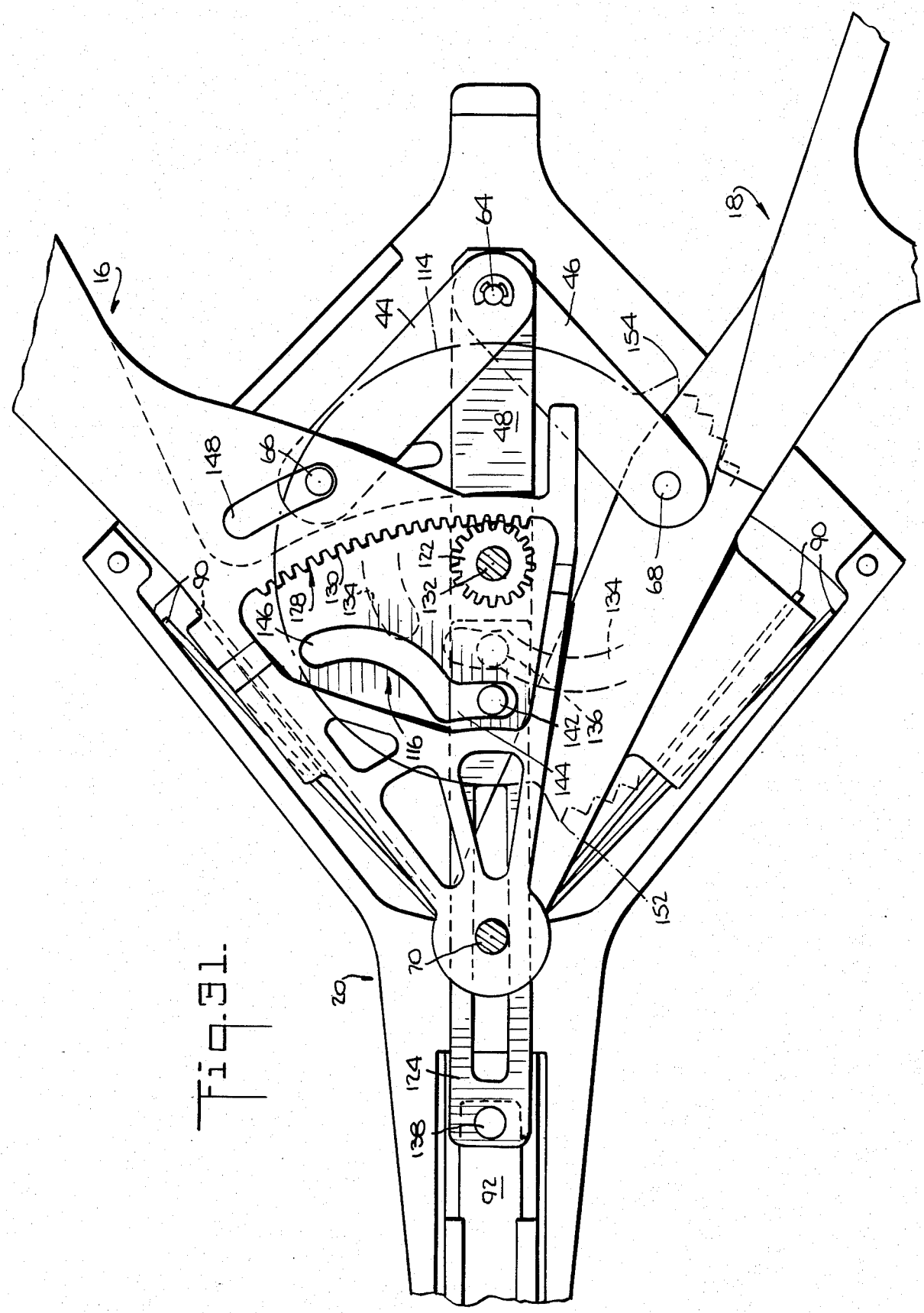
FIGS. 31–33 are plan sectional views, at the level of the instrument's right-hand feed handle, showing the configuration of the actuating and sequencing section at rest (FIG. 31), after feeding (FIG. 32) and after clip closure (FIG. 33).
Figure 32:
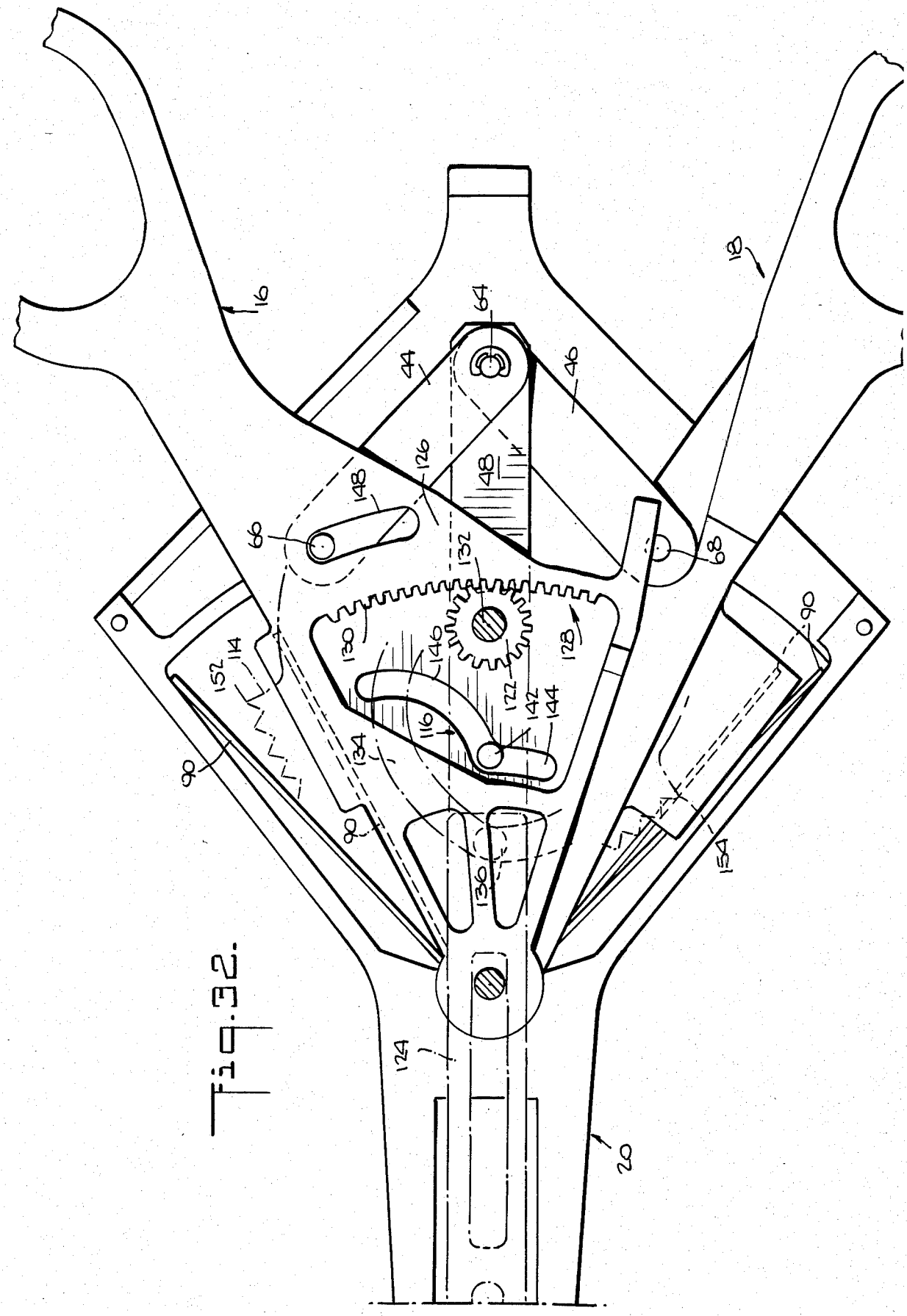

The first step—feeding—is accomplished through the movement of handle 16 inward from the position shown in FIG. 31 to the position shown in FIG. 32. This movement, by means of spur gear 122, rotatable cam 114 and cam follower 124, produces distal movement of feed ratchet 92 through its forward stroke (d+p+s), causing the forwardmost clip to move into jaws 12 and the remaining clips to index one step forward.

Figure 26:
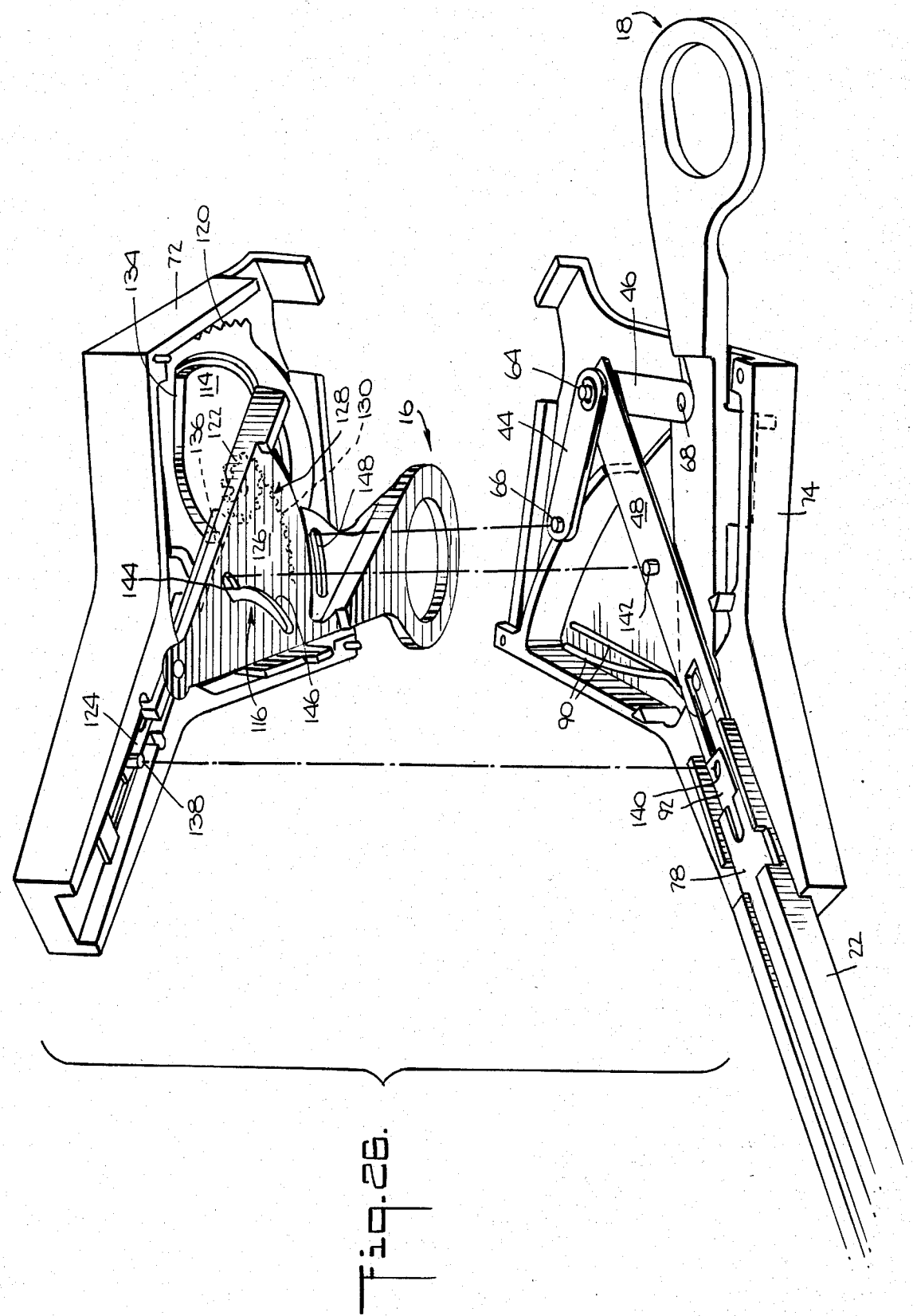
FIGS. 26 and 27 are exploded perspective views, with parts removed for clarity, of the actuating and sequencing section, showing the construction of that section and its connection to the clip storing, advancing, and deforming sections.
Figure 27:
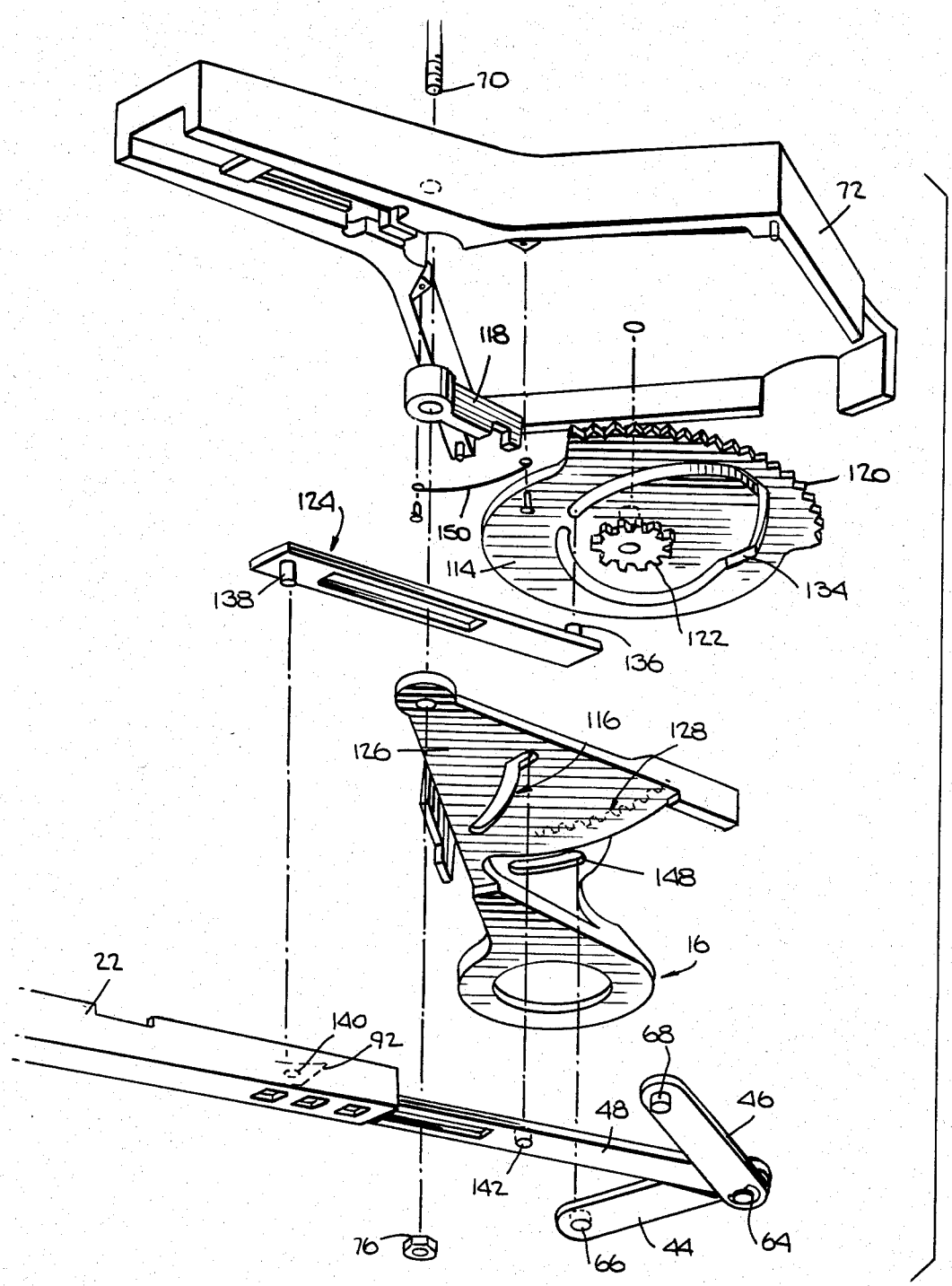
Figure 30:
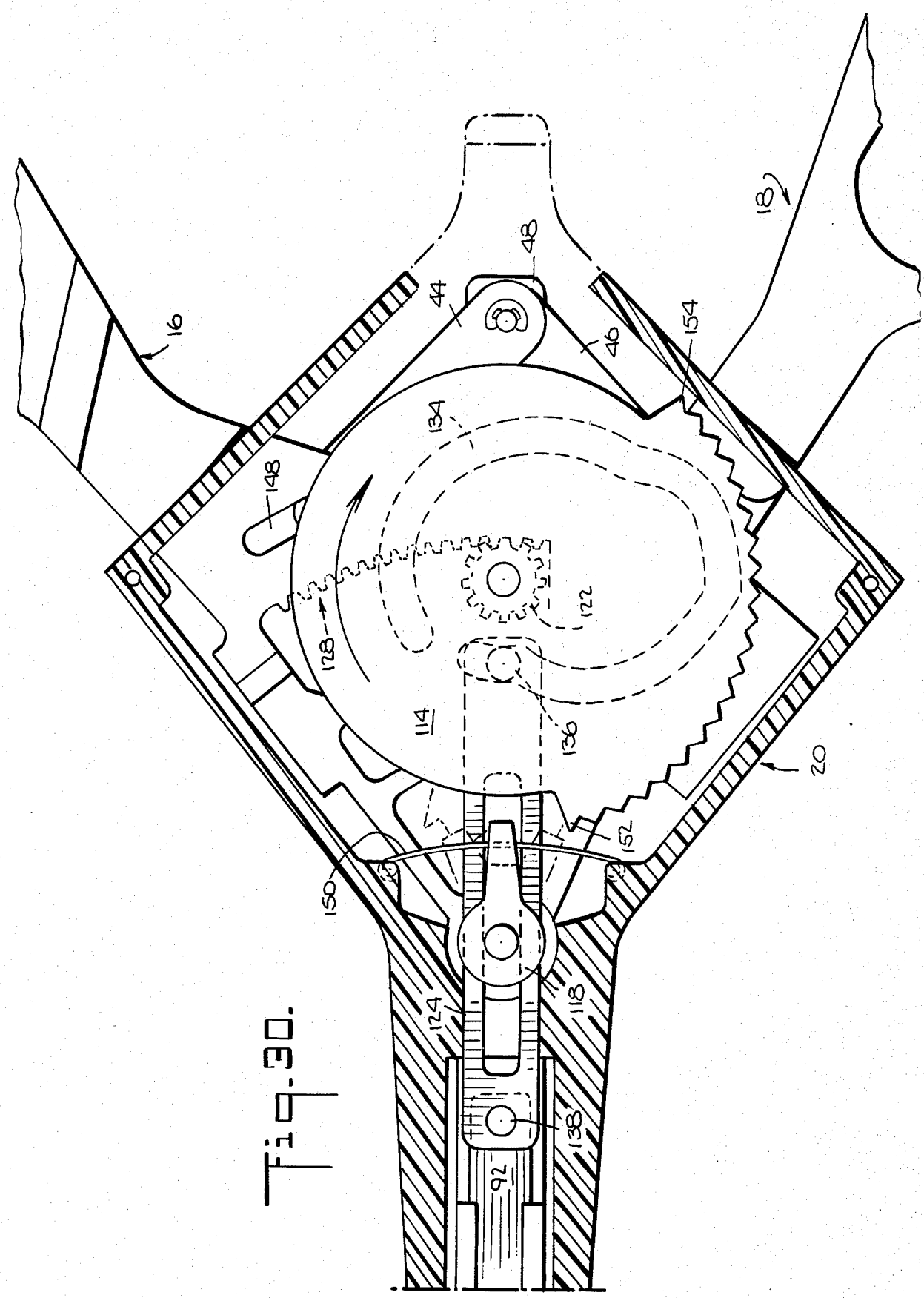
FIG. 30 is a plan cross-sectional view, at the level of the rotatable cam, showing the actuating and sequencing section in its at rest condition.

Handle 16 carries, on its inward projection 126, internal gear segment 128 having drive teeth 130 (FIGS. 26–27 and 31–33). These teeth mesh with spur gear 122 which is formed as part of rotatable cam 114, which itself is mounted for rotation about shaft 132 attached to the upper portion 72 of instrument housing 20 (FIG. 29). Included in the lower surface of cam 114 is cam path 134 shown in detail in FIG. 34. Riding in the cam path is stud 136 of cam follower 124 (FIG. 27). The other end of cam follower 124 is attached to feed ratchet 92 through stud 138 which mates with hole 140 in the feed ratchet.

As feed cam 114 rotates in response to inward movement of handle 16, it brings different portions of cam path 134 into engagement with stud 136 of cam follower 124. These portions of cam path 134 are at different distances from the axis of rotation of feed cam 114 (i.e., shaft 132) and thus cam follower 124 and the attached feed ratchet 92 move distally and proximally tracing out the radial locations of cam path 134 from the cam's axis of rotation.

Figure 34:
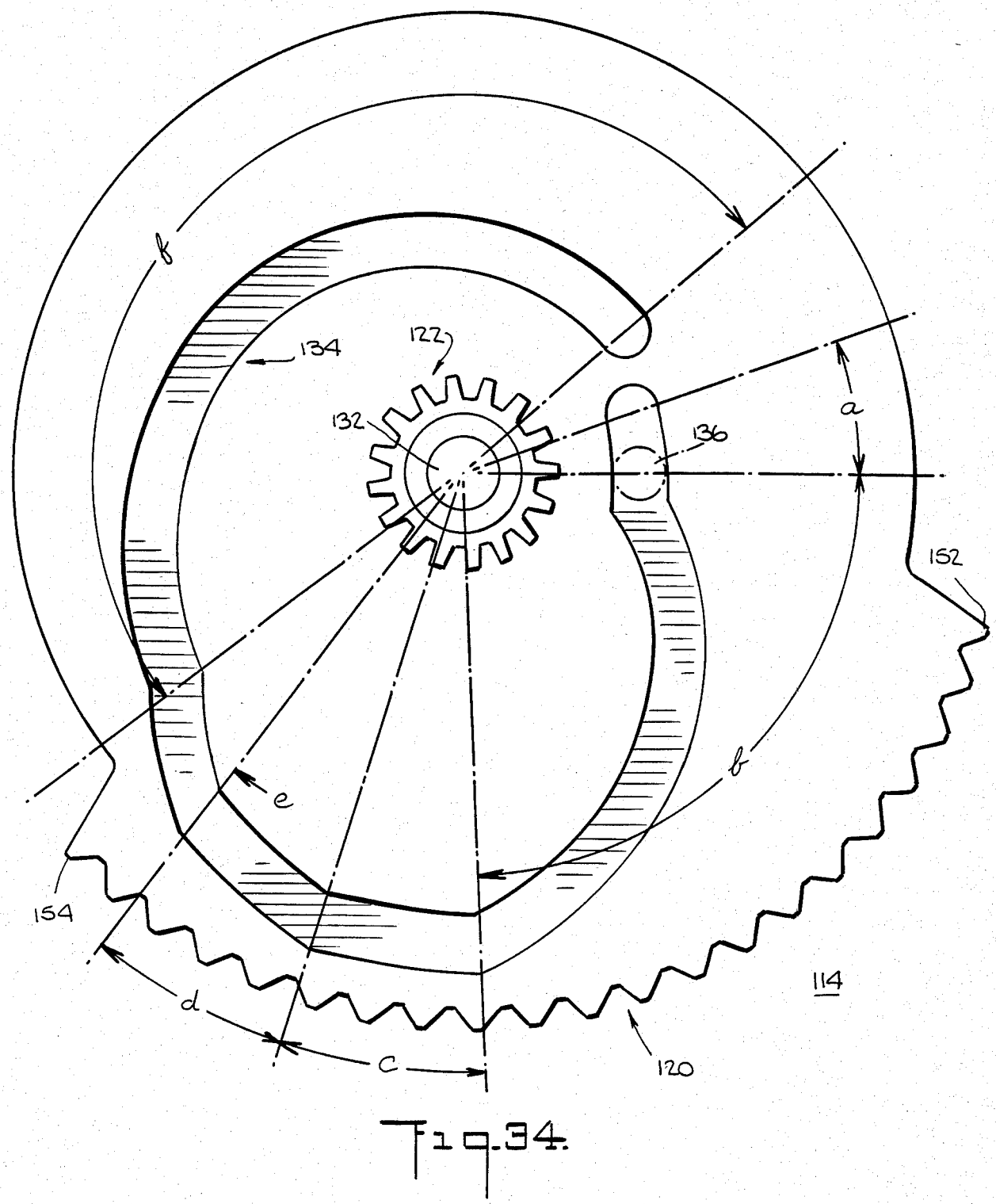
FIG. 34 is a detailed view of the rotatable cam of the instrument's actuating and sequencing section.

The detailed configuration of cam path 134 is shown in FIG. 34 where the complete path has been divided into six segments labelled a though f. Feeding is controlled by segments a, b, and c.

Segment a is located at a fixed distance from shaft 132 and provides a dwell period during which cam follower 124 and feed ratchet 92 remain stationary although handle 16 is moving inward. This period is used to compensate for manufacturing tolerances of the various parts which produce feeding and insures positive engagement of these parts when feeding actually commences.

The actual feeding occurs over segment b. Over this segment cam path 134 moves continuously outward from the cam's axis of rotation. Because cam follower 124 engages cam path 134 on the distal side of the axis of rotation, cam follower 124 and feed ratchet 92 move distally as cam follower stud 136 traces out this segment of the cam path. The radial locations of cam path 134 through this segment are such as to smoothly move feed ratchet 92 through its complete distal stroke (s+p+d), thus feeding a clip into jaws 12.

For reliable feeding, jaws 12 are held in their completely open position, ready to receive the forwardmost clip from the clip storing and advancing section, as feed ratchet 92 moves through its distal stroke. This is accomplished through the interaction of interlock pin 142 on jaw blade extension 48 with an initial segment 144 of sequencing slot 116 in handle 16 (FIG. 26).

Slot 116 comprises two segments, labelled 144 and 146 in FIG. 26. Segment 144 is spaced from the axis of rotation of handle 16 (i.e., shaft 70, FIG. 27) so as to hold interlock pin 142 stationary in its distal-most position as handle 16 rotates inward. The length of segment 144 corresponds to the angular movement of handle 16 needed to rotate cam 114 through segments a, b and c. Segment 146, on the other hand, allows jaw blade extension 48 to move proximally along the distal-proximal axis of the instrument to close the clip. The shape of segment 146 matches the rate of proximal movement of jaw blade extension 48 caused by inward movement of handles 16 and 18. Note that this rate of proximal movement varies with the location of jaw blade extension 48 because of the connection of handles 16 and 18 to the jaw blade extension through links 44 and 46.

By means of these two segments of sequencing slot 116, the clip deforming section is controlled so that jaws 12 remain in their completely open condition until feeding is completed, and only then move proximally to close the clip.

Handle 16 also includes a second sequencing slot 148 which mates with pin 66 on link 44. This slot allows handle 16 to move inward to produce clip feeding without the handle exerting inward force on link 44.

Segment c, which constitutes a dwell period for feed ratchet 92, provides a transition from clip feeding to clip closure as the clip deforming section unlocks through the passage of interlock pin 142 from segment 144 to segment 146 of sequencing slot 116. During this segment, cam path 134 is of constant radius and feed ratchet 92 stands still. The segment serves to compensate for manufacturing tolerances of the various parts which produce clip feeding and clip deformation and insures that clip deformation does not begin until feed ratchet 92 has been fully advanced.

Once segments a, b and c of cam path 134 have been traversed, clip deformation begins. During this process, the clip deforming section (including jaws 12, jaw blade 50 and jaw blade extension 48), clip carrier housing 78 and backstop ratchet 94, all move proximally together at the rate defined by the inward movement of handles 16 and 18 acting on jaw blade extension 48 through links 44 and 46. As described above, this proximal movement produces clip closure through the movement of cam surface 86 on each of jaw blade arms 50 relative to cam surface 88 on sleeve 22.

During clip closure, feed ratchet 92 also moves proximally, as cam follower 124 traces out segments d through f of cam path 134. The rate of proximal motion of feed ratchet 92 for two of these segments, d and f, is the same as the rate of motion of the other proximally moving elements. In segment e, however, feed ratchet 92 moves faster than the other elements. The functions of these segments are as follows.

Segment d constitutes the period of time during which cam surface 86 on each of the jaw blade arms moves back from its resting position and comes into contact with cam surface 88 on sleeve 22 in preparation for closing the clip. The radial distance of cam path 134 from the axis of rotation of cam 114 decreases during this segment, moving feed ratchet 92 back with jaws 12.

In segment e, feed ratchet 92 increases in speed relative to the other elements so as to move the forwardmost tooth 24 of that ratchet (the clip stop) proximally to accommodate the proximal movement of the apex of the clip as the clip is closed by the closing jaws. As discussed above, this means that feed ratchet 92 retraces part of the feed stroke. Thereafter, in segment f, feed ratchet 92 again moves proximally in synchrony with the other proximally moving elements, as the clip is clamped about the tissue.

Upon completion of clamping, the surgeon releases handles 16 and 18, whereupon springs 90 push the handles apart, returning the instrument to its initial condition. Specifically, the force produced by springs 90 causes feed ratchet 92, the clip deforming section, clip carrier housing 78 and backstop ratchet 94 to retrace the motions they followed during closing.

Initially feed ratchet 92 and the other distally moving elements move synchronously as segment f of cam path 134 is retraced. Then, through segment e, feed ratchet 92 moves distally faster than the other distally moving parts, so that, by the time segment d is reached, feed ratchet 92 and backstop ratchet 94 are again located, relative to each other, at the full feed position (i.e. feed ratchet 92 is distal of backstop ratchet 9 by the distance d+p+s). Next, feed ratchet 92 moves synchronously with the other parts as cam surfaces 86 and 88 move apart (segment d). Feed ratchet 92 then remains stationary, during segment c, as interlock pin 142 on jaw blade extension 48 moves into segment 144 of slot 116. Next, feed ratchet 92 moves proximally through segment b completing the return portion of the feed stroke (FIGS. 22 through 25). Finally, feed ratchet 92 comes to rest in the initial configuration (segment a).

To insure that the instrument is not operated out of sequence and to prevent jamming, the actuating and sequencing section includes the two-way clutch system mentioned above, comprising pawl 118 which pivots about shaft 70, pawl spring 150 and clutch teeth 120 on cam 114 (FIG. 27). Spring 150 holds pawl 118 against teeth 120 and causes it to act as an escapement ratchet for either direction of rotation of cam 114. Accordingly, once pawl 118 passes tooth 152 on cam 114 (FIG. 30), the instrument handles cannot be moved outward again until they have been moved inward far enough (1) to complete feeding and (2) to deform the clip which has been fed at least enough to guarantee that the clip will fall out of the jaws when the jaws return to their open, resting condition. This insures that the clips are fully indexed forward and prevents feeding of a clip into the jaws while the jaws are still holding a previously fed clip.

The pawl-clutch teeth combination also insures proper sequencing during resetting of the instrument. Once pawl 118 passes tooth 154 on cam 114 (FIG. 30), upon release of handles 16 and 18 after the clip has been deformed, the handles cannot be moved inward again until the instrument has completely returned to its initial, resting condition. Segment 146 of sequencing slot 116 also insures proper sequencing during resetting by guaranteeing that handle 16 retraces the clip deforming portion of its motion before retracing the clip feeding portion. That is, handle 16 is not free to move outward along slot 148 until interlock pin 142 on jaw blade extension 48 has retraced segment 146 of slot 116 (the clip deformation portion) and has reached segment 144 (the clip feeding portion).

The clutch system, which locks at each tooth, also allows the surgeon to release his inward pressure against reset springs 90 while placing a clip about the tissue to be clamped.

The components of this instrument are preferably made of materials designed to produce an inexpensive, disposable instrument. Thus, housing 20, handles 16 and 18, rotatable cam 114 and clip carrier housing 78 can be made of an inexpensive, lightweight material, such as an ABS plastic. Sleeve 22 and the clip deforming section, including jaws 12, jaw blade 50, jaw blade extension 48 and links 44 and 46, can be made of stainless steel. Of course, other suitable materials can be used.

It is to be understood that although a preferred embodiment of this invention has been described, other embodiments varying from that shown can be employed without departing from the spirit and scope of the invention. For example, rather than resetting feed ratchet 92 relative to backstop ratchet 94 after jaws 12 return to their open position, the feed ratchet could be reset before or simultaneously with the opening of jaws. Also, in the resting state a clip could be in jaws 12, feeding occurring during resetting of the instrument. In such a case, the first operation caused by movement of the handles would be closing jaws 12, rather than feeding. Similarly, rather than camming both jaws 12 closed, one jaw could be held stationary and the other jaw cammed towards the stationary jaw, in which case, cam surfaces would only be associated with the moving jaw.

We claim:

1. Apparatus for applying hemostatic clips to tissue comprising:

a body;

means associated with the body for storing a plurality of undeformed hemostatic clips having elongated, spaced-apart arms;

a pair of jaws at one end of the body for receiving, holding and deforming a clip, the jaws being movable relative to each other in their common plane to deform the clip by bringing the spaced-apart arms of the clip towards one another;

means for camming the jaws closed including first cam surface means associated with the body, second cam surface means associated with the jaws, and means for moving the first and second cam surface means relative to each other to cause the jaws to move towards one another in their common plane to deform a clip;

means for feeding one clip at a time from the means for storing to the jaws; and actuating and sequencing means for sequentially actuating the means for feeding and the means for camming the jaws closed including a pair of handles movable between a first open position and a second closed position, movement of said handles from said first open position to said second closed position first causing the means for feeding to move a clip from the means for storing to the jaws and then causing the means for camming the jaws closed to move the jaws towards each other to close the clip.

2. The apparatus of claim 1 wherein the body includes an elongated sleeve extending towards the jaw end of the apparatus and the first cam surface means for closing the jaws is associated with the jaw end of the sleeve.

3. The apparatus of claim 2 wherein at least a portion of the sleeve is longitudinally curved.

4. The apparatus of claims 2 or 3 wherein the means for storing extends along at least a portion of the sleeve and the undeformed clips are held one behind the other with their arms pointing towards the jaw end of the sleeve.

5. Apparatus for applying hemostatic clips to tissue comprising:
a body;
means associated with the body for storing a plurality of undeformed hemostatic clips having elongated, spaced-apart arms;
a pair of jaws at one end of the body which are movable towards each other in their common plane for deforming a clip by bringing the spaced-apart arms of the clip towards one another, the jaws having a first, spaced-apart position for receiving and holding a clip;
means for camming the jaws closed including first cam surface means associated with the body, second cam surface means associated with the jaws, and means for moving the first and second cam surface means relative to each other to cause the jaws to move towards one another in their common plane to deform a clip;
means for returning the jaws to their first, spaced-apart position after they have been cammed closed by the means for moving the cam surface means relative to each other;
means for feeding one clip at a time from the means for storing to the jaws, the means moving from a first position to a second position as the clip is fed into the jaws;
means for returning the means for feeding to its first position after the clip has been fed; and
actuating and sequencing means for sequentially applying the plurality of hemostatic clips including a pair of handles movable between a first, open position and a second closed position, movement of said handles from said first open position to said second closed position causing the means for feeding to move from its first position to its second position to feed a clip into the jaws and causing the means for camming to close the jaws, movement of said handles from said second closed position to said first open position actuating the means for returning the jaws to their first, spaced-apart position and the means for returning the means for feeding to its first position after a clip has been deformed by the jaws.

6. The apparatus of claim 5 wherein the actuating and sequencing means includes a clutch mechanism which prevents the jaws from returning to their first, spaced apart position until after the jaws have been cammed closed sufficiently far to insure that any clip in the jaws will fall out of the jaws, when the jaws return to their first, spaced apart position.

7. The apparatus of claim 6 wherein the clutch mechanism also prevents feeding until after the means for feeding has returned to its first position.

8. The apparatus of claims 5, 6, or 7 wherein the means for storing includes first and second ratchets located adjacent each other to form a space for the clips, the ratchets having teeth thereon for engagement with the clips, the teeth being directed into the space between the ratchets and facing towards the jaw end of the apparatus, and the means for feeding includes means for moving the first ratchet relative to the second ratchet in the direction of the jaws to feed the clip closest to the jaws into the jaws and to index each of the remaining clips one tooth on the second ratchet closer to the jaws.

9. The apparatus of claim 8 wherein the first ratchet moves relative to the second ratchet in the direction of the jaws by a distance greater than the spacing between ratchet teeth and less than twice the spacing between ratchet teeth.

10. The apparatus of claim 8 wherein the body includes an elongated sleeve extending towards the jaw end of the apparatus, the sleeve includes at its jaw end the first cam surface means for camming the jaws closed, and at least a portion of each of the first and second ratchets is within the sleeve.

11. The apparatus of claim 10 wherein at least a portion of the sleeve is longitudinally curved, at least a part of the portion of each ratchet which is within the sleeve is in the curved portion of the sleeve, and the ratchet teeth associated with the part of each ratchet in the curved portion of the sleeve are sized and spaced to accommodate the curve so that the clip engaging portions of the teeth are essentially uniformly spaced along the length of the ratchet and the clip engaging portions extend into the space between the ratchets sufficiently far to positively engage the clips, notwithstanding the curve.

12. The apparatus of claim 11 wherein the spacing of the teeth on the first ratchet is substantially uniform along the entire length of the first ratchet;
the amount by which the teeth on the first ratchet extend into the space between the first and second ratchets is substantially uniform along the entire length of the first ratchet;
the spacing of the teeth on the second ratchet is substantially uniform along the entire length of the second ratchet; and
the amount by which the teeth on the second ratchet extend into the space between the first and second ratchets is substantially uniform along the entire length of the second ratchet.

13. The apparatus of claim 8 wherein the actuating and sequencing means includes a rotatable cam connected to the means for moving the first ratchet.

14. The apparatus of claim 13 wherein the cam first causes the first ratchet to move toward the jaws to feed the leading clip into the jaws and to index the remaining clips one tooth on the second ratchet closer to the jaws, and then causes the first ratchet to move away from the jaws so as to be out of interference with the jaws as they close.

15. The apparatus of claim 1 or 5 wherein the actuating and sequencing means includes a rotatable cam connected to said means for feeding.

16. The apparatus of claim 15 wherein said rotatable cam causes said means for feeding first to move toward the jaws to feed a clip to the jaws and then to move away from the jaws so as to be out of interference with the jaws as they close.

17. The apparatus of claims 1 or 5 wherein the means for storing is located adjacent the jaws of the instrument and moves with the means for moving the first and second cam surface means relative to each other so as to be out of interference with the jaws as they close.

18. Apparatus for applying hemostatic clips to tissue comprising:
a body including an elongated sleeve which extends along the distal-proximal axis of the apparatus;
means within at least a portion of the sleeve for storing a plurality of undeformed hemostatic clips having elongated, spaced-apart arms, the means including first and second ratchets located adjacent to each other to form a space for the clips, the ratchets having teeth thereon for engagement with the clips, the teeth being directed into the space between the ratchets and facing towards the distal end of the apparatus;
a pair of jaws at the distal end of the sleeve, the jaws having a first, spaced-apart position for receiving and holding a clip and being movable toward each other in their common plane for deforming a clip by bringing the spaced-apart arms of the clip towards one another;
means for moving the first ratchet relative to the second ratchet from a first position to a second position to feed the clip closest to the jaws into the jaws and to index each of the clips remaining in the means for storing one tooth on the second ratchet closer to the jaws;
means for camming the jaws closed including first cam surface means associated with the distal end of the sleeve, second cam surface means associated with the jaws, and means for moving the first and second cam surface means relative to each other to cause the jaws to move towards one another in their common plane to deform a clip;
means for returning the jaws to their first, spaced-apart position after they have been cammed closed by the means for moving the cam surface means relative to each other;
means for returning the first ratchet to its first position after the clip closest to the jaws has been fed and the remaining clips indexed; and
actuating and sequencing means for sequentially applying the plurality of hemostatic clips including a pair of handles movable between a first open position and a second closed position, movement of said handles from said first open position toward said second closed position actuates in sequence first the means for moving the first ratchet from its first to its second position, and then the means for moving the first and second cam surface means relative to each other, movement of said handles from said second closed position to said first open position actuates in sequence first the means for returning the jaws to their first, spaced-apart position and then the means for returning the first ratchet to its first position after a clip has been deformed by the jaws.

19. The apparatus of claim 18 wherein the actuating and sequencing means includes a rotatable cam connected to said means for moving said first ratchet.

20. The apparatus of claim 19 wherein said rotatable cam causes said first ratchet first to move toward the jaws to feed a clip to the jaws and then to move away from the jaws so as to be out of interference with the jaws as they close.

21. The apparatus of claim 18 wherein the actuating and sequencing means includes clutch mechanism which prevents the jaws from returning to their first, spaced-apart position until after the jaws have been cammed closed sufficiently far to insure that any clip in the jaws will fall out of the jaws, when the jaws return to their first, spaced-apart position.

22. The apparatus of claim 21 wherein the clutch mechanism also prevents feeding until after the first ratchet has returned to its first position.

23. The apparatus of claim 15 wherein at least a portion of the sleeve is longitudinally curved.

24. The apparatus of claims 18, 21, 12 or 23 wherein the second ratchet moves with the means for moving the first and second cam surface means relative to each other, and the actuating and sequencing means includes a rotatable cam connected to the means for moving the first ratchet so as first to cause the first ratchet to move from its first to its second position and then to cause the first ratchet to move in relation to the movement of the second ratchet so that the first ratchet does not return to its first position until the jaws have closed and have returned to their first, spaced-apart position.

25. The apparatus of claim 24 wherein the handles are operatively connected to the rotatable cam and the means for moving the first and second cam surface means relative to each other, the handles being engageable by one hand and being movable from said first open position through an intermediate position to said second closed position with clip feeding occurring as the handles move from the first open position to the intermediate position and clip closure occurring as the handles move from intermediate position to the second closed position.

26. The apparatus of claim 25 wherein the connection to the rotatable cam is by means of a gear segment associated with the handles mating with a spur gear associated with the rotatable cam.

27. The apparatus of claim 25 wherein the handles include a sequencing slot associated with the means for moving the first and second cam surface means relative to each other which prevents that means from being actuated until feeding has been completed.

28. The apparatus of claim 27 wherein the handles include a second sequencing slot associated with the means for moving the first and second cam surface means relative to each other which permits the handles to produce rotation of the rotatable cam without actuation of the means for moving the first and second cam surface means relative to each other.

29. The apparatus of claims 5 or 18 wherein the jaws are associated with a pair of movable arms, the arms being spaced from each other, when unconstrained, by a distance such that the spacing between the jaws is less than the spacing between the jaws in the first, spaced-apart position, and the apparatus further comprises means associated with the arms and the body for increasing the spacing between the arms to bring the jaws to their first, spaced-apart position.

30. The apparatus of claim 29 wherein the means for increasing the spacing between the jaws includes projections associated with the arms which engage the body to bring the jaws to their first, spaced-apart position.

31. The apparatus of claim 30 wherein the projections pass through openings in the body and engage the outer surface of the body.

32. The apparatus of claims 1, 5 or 18 further comprising means for resisting movement of a fed clip away from the front of the jaws during positioning of the apparatus relative to the tissue to which the clip is to be applied.

33. Hemostatic clip applying apparatus comprising:
a body;
a pair of jaws at one end of the body, the jaws having a first, spaced-apart position for receiving and holding a clip and being movable towards each other from the first, spaced-apart position for deforming a clip;
a pair of arms carrying the jaws, the arms being movable towards each other and being spaced from each other, when unconstrained, by a distance such that the spacing between the jaws is less than the spacing between the jaws in the first, spaced-apart position; and
means associated with the arms and the body for increasing the spacing between the arms to bring the jaws to their first, spaced-apart position.

34. The apparatus of claim 33 wherein the means for increasing the spacing between the jaws includes projections associated with the arms which engage the body to bring the jaws to their first, spaced-apart position.

35. The apparatus of claim 34 wherein the projections pass through openings in the body and engage the outer surface of the body.

* * * * *